United States Patent [19]

Masegi et al.

[11] Patent Number: 5,028,420
[45] Date of Patent: Jul. 2, 1991

[54] MUTEINS OF TUMOR NECROSIS FACTOR

[75] Inventors: Tsukio Masegi, Hino; Satoshi Nakamura; Kazuo Kitai; Masami Fukuoka; Kenji Yone, all of Hino; Arata Kato, Sayama; Jun Suzuki, Tokyo; Noriyuki Tsunekawa, Hino; Yataro Ichikawa, Tokorozawa, all of Japan

[73] Assignee: Teijin Limited, Osaka, Japan

[21] Appl. No.: 235,576

[22] Filed: Jul. 26, 1988

[30] Foreign Application Priority Data

Apr. 28, 1988 [JP] Japan ................... 63-104222

[51] Int. Cl.$^5$ ............... C07K 13/00; A61K 37/02
[52] U.S. Cl. ................... 424/85.1; 530/351; 435/69.5; 435/320.1; 536/27
[58] Field of Search ............ 530/351; 424/85.1

[56] References Cited

U.S. PATENT DOCUMENTS 4,677,063 6/1987 Mark ........................... 435/68

OTHER PUBLICATIONS

Tavernier, J. et al., "Isolation and Expression of the Genes Coding for Mouse & Human Tumor Necrosis Factor..." Lymphobines, vol. 3, pp. 181–188, 1987.

Primary Examiner—Lester L. Lee
Assistant Examiner—Nina Ossanna
Attorney, Agent, or Firm—Wenderoth, Lind & Ponack

[57] ABSTRACT

A novel physiologically active polypeptide having antitumor activity obtained by improving human tumor necrosis factor (TNF). The amino acid sequence of the polypeptide essentially corresponds to that of human tumor necrosis factor, except that ten amino acids Nos. 1 to 10 are deleted and $(Met)_n$-Arg-Lys-Arg are added to the amino ($NH_2$)-terminus, where n is 0 or 1. Other amino acid modifications can also be made to the polypeptide while retaining high antitumor activity. The novel polypeptide has less side effects that the natural-type TNF, particularly with respect to cytotoxicity. A a DNA fragment encoding the polypeptide, a recombinant plasmid containing the DNA fragment, a recombinant microorganism cell transformed with the plasmid, a method of producing a novel physiologically active polypeptide using the microorganism cell, and a pharmaceutical composition comprising the polypeptide as an active ingredient are also provided.

4 Claims, 15 Drawing Sheets

```
ClaI
 |
TCG-ATA-ATG-GTC-AGG-TCA-TCT-TCA-CGA-ACC-CCG-AGT-GAC-AAG-CCT-GTA-GCC-CAT-GTT-GTA
    (MET)Val-Arg-Ser-Ser-Ser-Arg-Thr-Pro-Ser-Asp-Lys-Pro-Val-Ala-His-Val-Val
         1                              10

GCA-AAC-CCT-CAA-GCT-GAG-GGG-CAG-CTC-CAG-TGG-CTG-AAC-GCC-CGG-GCC-AAT-GCC-CTG-CTG
Ala-Asn-Pro-Gln-Ala-Glu-Gly-Gln-Leu-Gln-Leu-Trp-Leu-Asn-Ala-Arg-Ala-Asn-Ala-Leu-Leu
         20                              30

GCC-AAT-GGC-GTG-GAG-CTG-AGA-GAT-AAC-CAG-CTG-GTG-GTA-CCA-TCA-GAG-GGC-TTG-TAC-CTC
Ala-Asn-Gly-Val-Glu-Leu-Arg-Asp-Asn-Gln-Leu-Val-Val-Pro-Ser-Glu-Gly-Leu-Tyr-Leu
         40                              50

ATT-TAC-TCC-CAG-GTC-CTC-TTC-AAG-GGC-CAA-GGC-TGC-CCG-TCG-ACC-CAT-GTG-CTC-CTC-ACC
Ile-Tyr-Ser-Gln-Val-Leu-Phe-Lys-Gly-Gln-Gly-Cys-Pro-Ser-Thr-His-Val-Leu-Leu-Thr
         60                              70

CAC-ACC-ATC-AGC-CGC-ATC-GCC-GTC-TCC-TAC-CAG-ACC-AAG-GTC-AAC-CTC-CTC-TCT-GCG-ATC
His-Thr-Ile-Ser-Arg-Ile-Ala-Val-Ser-Tyr-Gln-Thr-Lys-Val-Asn-Leu-Leu-Ser-Ala-Ile
         80                              90

AAG-AGC-CCC-TGC-CAG-AGG-GAG-ACC-CCA-GAG-GGG-GCT-GAG-GCC-AAG-CCA-TGG-TAT-GAG-CCC
Lys-Ser-Pro-Cys-Gln-Arg-Glu-Thr-Pro-Glu-Gly-Ala-Glu-Ala-Lys-Pro-Trp-Tyr-Glu-Pro
         100                             110

ATC-TAT-CTG-GGA-GGG-GTC-TTC-CAG-CTG-GAG-AAG-GGT-GAC-CGA-CTC-AGC-GCT-GAA-ATC-AAT
Ile-Tyr-Leu-Gly-Gly-Val-Phe-Gln-Leu-Glu-Lys-Gly-Asp-Arg-Leu-Ser-Ala-Glu-Ile-Asn
         120                             130

CGG-CCC-GAC-TAT-CTC-GAC-TTT-GCC-GAG-TCT-GGG-CAG-GTC-TAC-TTT-GGG-ATT-ATT-GCC-CTG
Arg-Pro-Asp-Tyr-Leu-Asp-Phe-Ala-Glu-Ser-Gly-Gln-Val-Tyr-Phe-Gly-Ile-Ile-Ala-Leu
         140                             150

HindIII
  |
TGA-TAA-GCT
***-***
```

FIG. I PRIOR ART

```
CGATAATGGTGTCAGGTCATCTTCACGAACCCCGAGTGACAAGCCTGTAGCCCATGTTGTAGCAAACCCTCAAGCTGAGGGGC
         TATTACCAGTCCAGTAGAAGTGCTTGGGGCTCACTGTTCGGACATCGGGTACAACATCGTTTGGGAGTTCGACTCCCCG
              └────TNF-1────┘                                └────TNF-2────┘

AGCTCCAGTGGCTGAACCCGCGGCCAATGCCCTGCTGTGGCCAATGGCGTGGAGCTGAGAGATAACCAGCTGGTGGTACCAT
    TCGAGGTCACCGACTTGGGCGCCGGTTACGGACGACACTCGGACTCTCTATTGGTCGACCACCATGGTA
    └────TNF-3────┘                          └────TNF-5────┘
                    └────TNF-4────┘

CAGAGGGCTTGTACCTCATTTACTCCCAGGTCCTCTTCAAGGGCCAAGGCTGCCCGTCGACCATGTGCTCCTCACCCACA
      GTCTCCCGAACATGGAGTAAATGAGGGTCCAGGAGAAGTTCCCGGTTCCGACGGGCAGCTGGTACACGAGGAGTGGGTGT
       └────TNF-6────┘                           └────TNF-7────┘

CCATCAGCCGCGCATCGCCGTCTCCTACCAGACCAAGGTCAACCTCCTCTGCGATCAAGAGACCCCTGCCAGAGGGAGACCC
   GGTAGTCGGCGTAGCGGCAGAGGATGGTCTGGTTCCAGTTGGACGAGTTCTCGGGGACGGTCTCCCTCTGGG
   └────TNF-8────┘                         └────TNF-10────┘
              └────TNF-9────┘                        └────TNF-11────┘

┌────TNF-14────┐
CAGAGGGGCTGAGGCCAAGCCTATGAGCCCATCTATCTGGGAGGGGTCTTCTTCAGCTGGAGAAGGGTGACCGACTCA
       GTCTCCCCGACTCCGGTTCGGTACCATACTCGGGTAGATAGACCCTCCCAGAAGGTGACCTCTTCCCACTGGCTGAGT
       └────TNF-12────┘                      └────TNF-16────┘
                └────TNF-13────┘

┌────TNF-14────┐
GCGCTGAAATCAATCGGGCCCGACTATCTCGACTTTGCCGAGTCTGGGCAGGTCTACTTTGGGATTATTGCCCTGTGATA
      CGCGACTTTAGTTAGCGGCCGGGCTGATAGAGCTGAAACGGCTCAGACCCGTCCAGATGAAACCCTAATAACGGGACACTATTCGA
      └────TNF-15────┘                       └────TNF-17────┘
```

FIG.2

FIG. 7-A
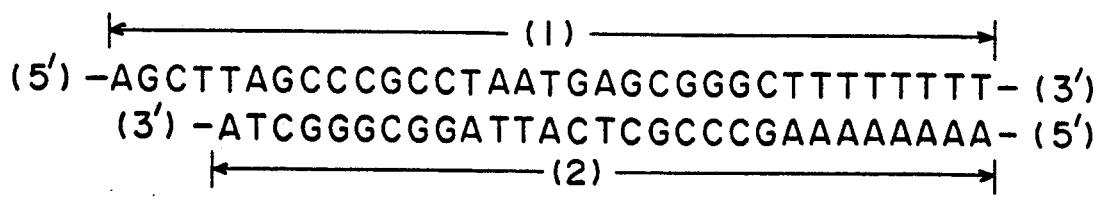
FIG. 7-B
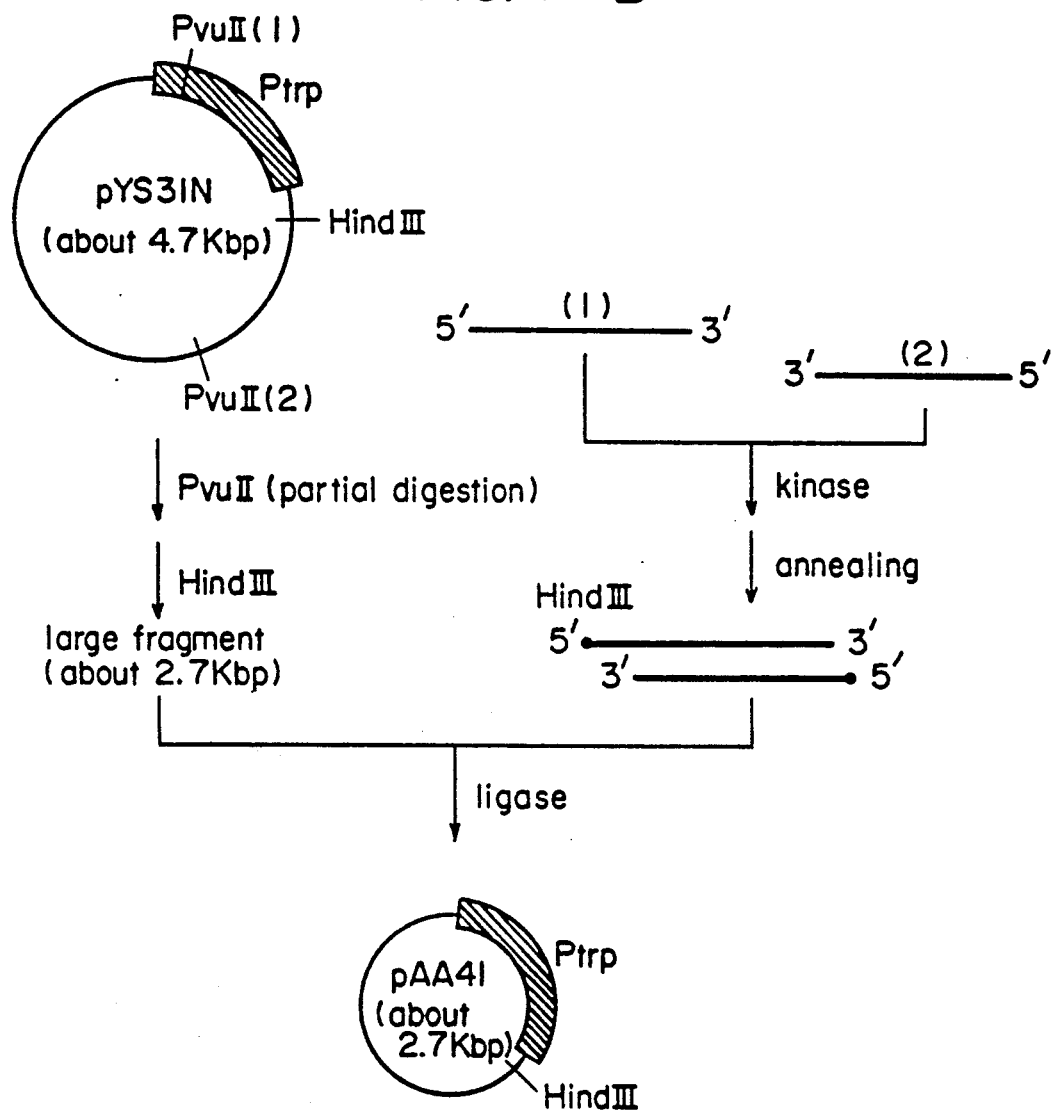

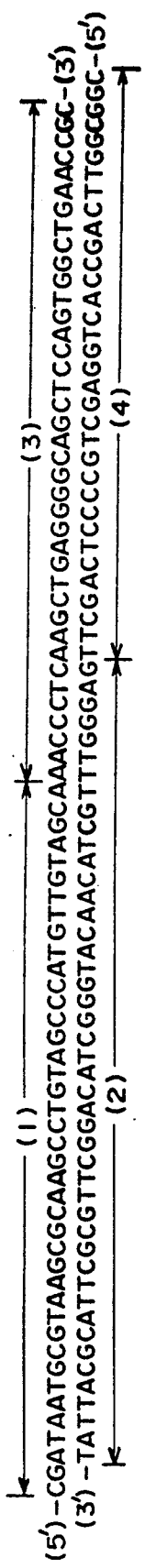
FIG. 9-A
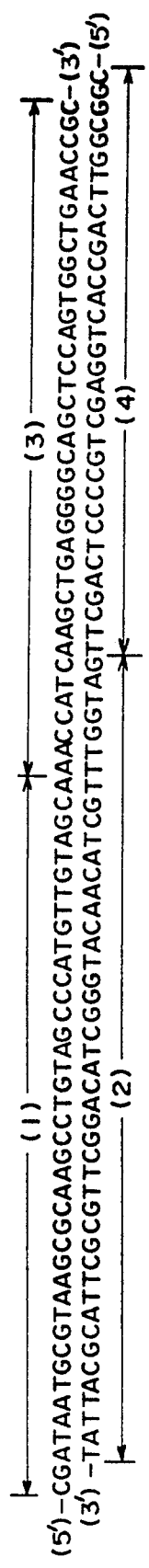
FIG. 14
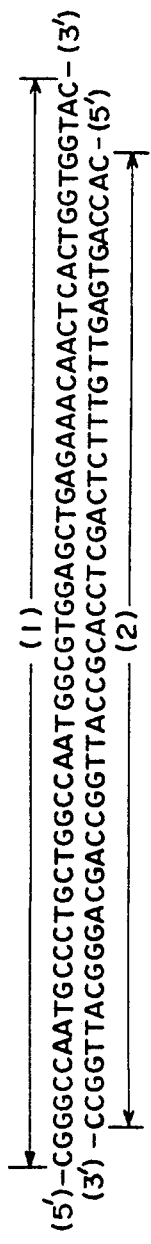
FIG. 15-A

FIG. 9-B
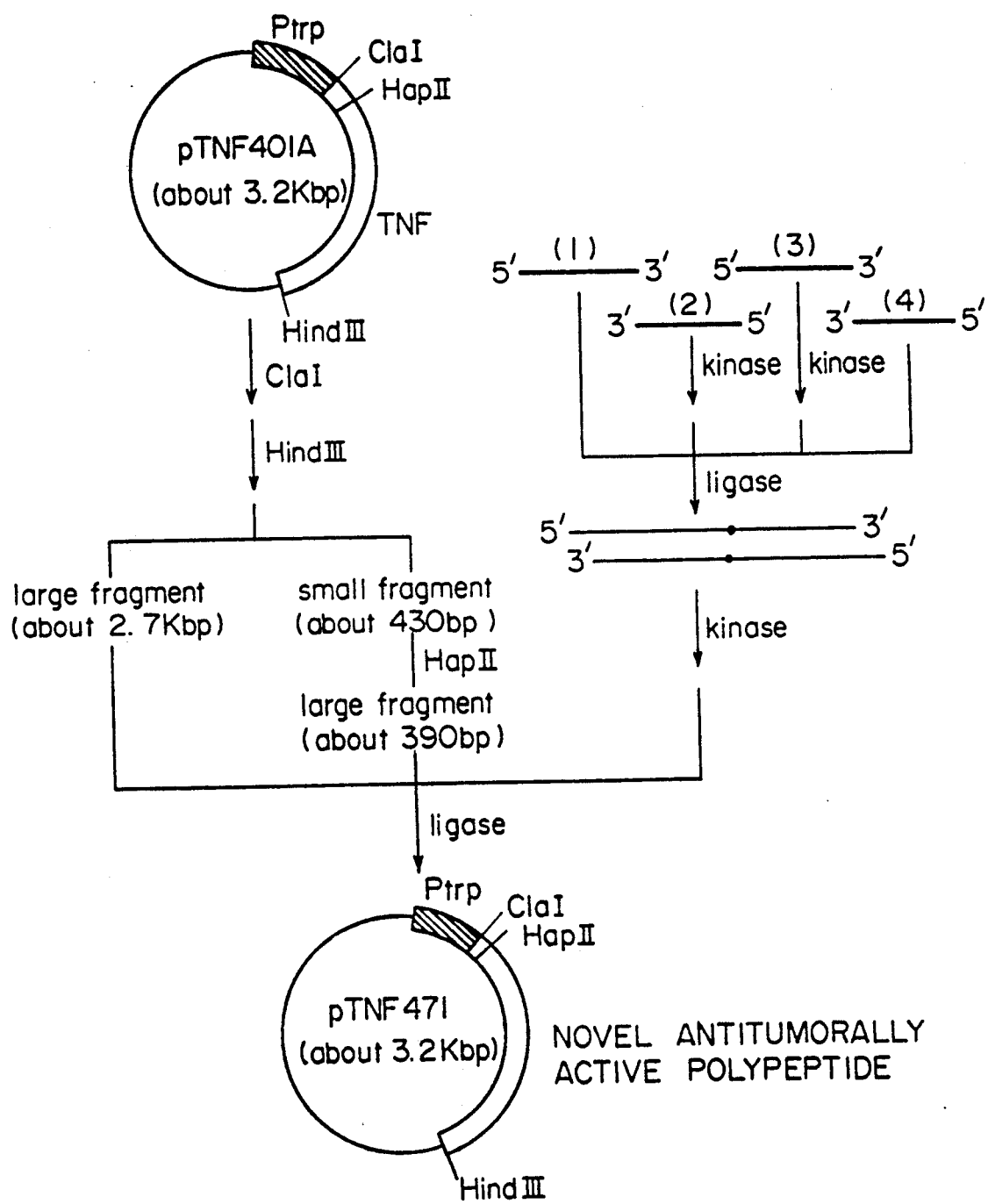

FIG. 15-B
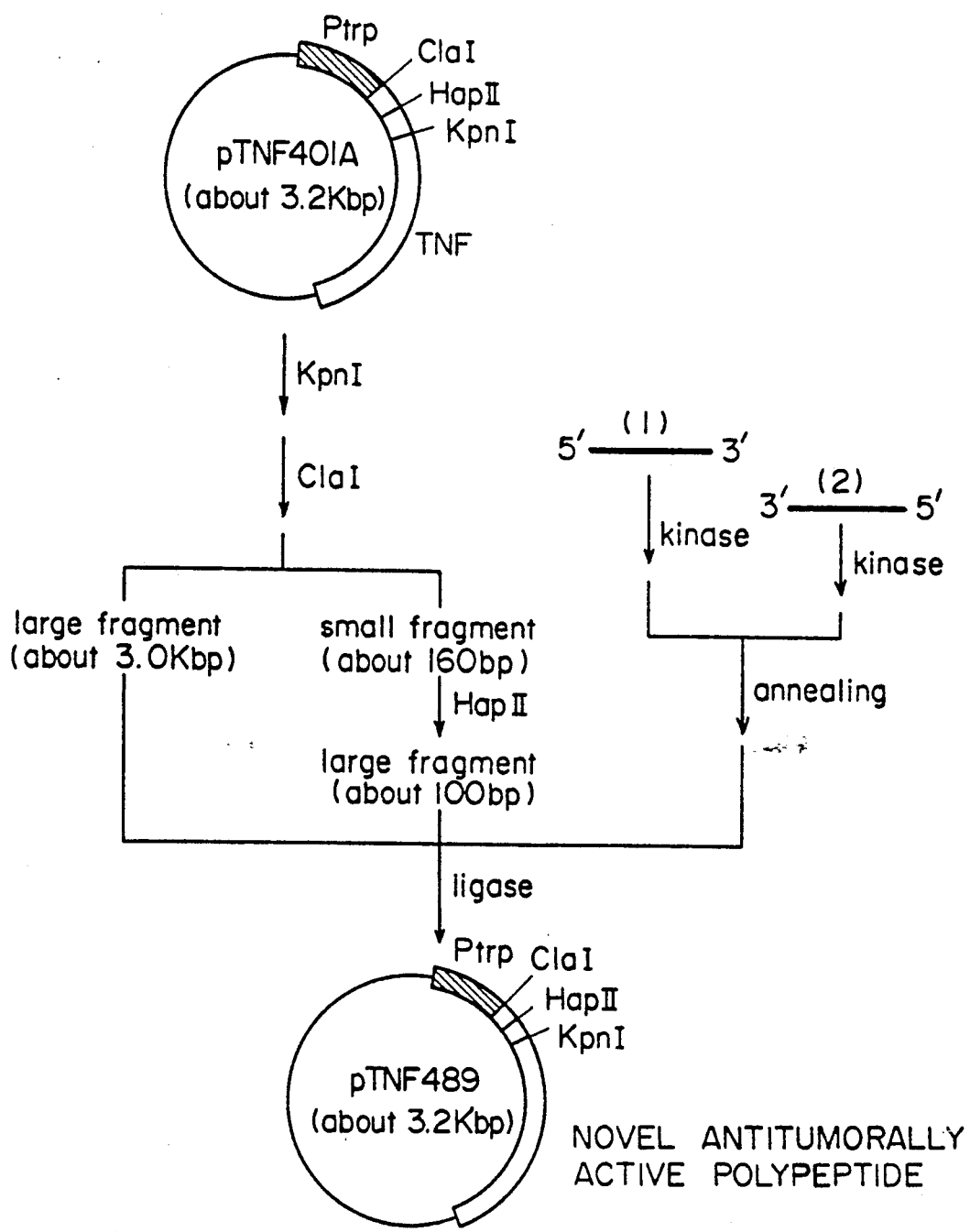

MUTEINS OF TUMOR NECROSIS FACTOR

This invention relates to a novel physiologically active polypeptide, a DNA fragment encoding the polypeptide, a recombinant plasmid containing the DNA fragment, a recombinant microorganism cell transformed with the plasmid, a method of producing a novel physiologically active polypeptide using the microorganism cell, and a pharmaceutical composition comprising the polypeptide as an active ingredient.

More specifically, it relates to a novel polypeptide having antitumor activity, a DNA fragment encoding the polypeptide, a recombinant plasmid containing the DNA fragment, a recombinant microorganism cell transformed with the plasmid, a method of producing the novel antitumorally active polypeptide using the microorganism cell, and to a pharmaceutical composition comprising the polypeptide as an active ingredient.

In the present specification and claims, the amino acid seqeunce and the polypeptide will be described and abbreviated by the method accepted by the Committee on Biochemical Nomenclature of IUPAC-IUB, and for example, the following abbreviations are used.

Ala: L-alanine
Arg: L-arginine
Asn: L-asparagine
Asp: L-aspartic acid
Cys: L-cysteine
Gln: L-glutamine
Glu: L-glutamic acid
Gly: glycine
His: L-histidine
Ile: L-isoleucine
Leu: L-leucine
Lys: L-lysine
Met: L-methionine
Phe: L-phenylalanine
Pro: L-proline
Ser: L-serine
Thr: L-threonine
Trp: L-tryptophan
Tyr: L-tyrosine
Val: L-valine A DNA fragment will be expressed by the bases contained in deoxyribonucleotides constituting it, and for example, the following abbreviatations are used.

A: adenine (representing deoxyadenylic acid)
C: cytosine (representing deoxycytidylic acid)
G: guanine (representing deoxyguanylic acid)
T: thymine (representing deoxythymidylic acid)

(H$_2$N)- and -(COOH) respectively show the amino-terminus and carboxy-terminus of an amino acid sequence, and (5')- and (3')- respectively show the 5'-terminus and the 3'-terminus of a DNA sequence. Carswell et al. found that a serum sample taken from a mouse stimulated with Bacillus Calmette-Guerin (BCG) and then given an endotoxin contains a substance which bleeds and necrotizes a solid tumor caused by a transplanted Meth A sarcoma; and they named this substance tumor necrosis factor (abbreviated as "TNF") [E. A. Carswell et al., Proc. Natl. Acad. Sci., U.S.A. 72, 3666 (1975)]. TNF is found in many animals such as mice, rabbits and humans. Since it acts specifically on tumor cells of any species, it is expected to be used as an antitumor agent.

Recently, Pennica et al. disclosed the primary structure of a human TNF protein by cloning cDNA of human TNF, and reported on the expression of the human TNF gene in *Escherichia coli* [D. Pennica et al.: Nature, 312, 724 (1984)]. Later, Shirai et al. [T. Shirai et al.: Nature, 313, 803 (1985)], Somura et al. Somura et al.: Cancer and Chemotherapy, 12, 160 (1985)], Wang et al. [A. M. Wang et al.: Science, 228, 149 (1985)), and Marmenout et al. A. Marmenout et al.: Eur. J. Biochem., 152, 515 (1985)] reported the expression of human TNF genes in *E. coli*.

Thus, large quantities of pure human TNF proteins have become available by using the recombinant DNA technology, and the antitumor activity and other physiological activities of TNF have been elucidated in more detail. For example, it was suggested that cachectin, a substance which is one cause of inducing cachexia in patients in the terminal stage of cancer or patients with serious infections, is very similar to TNF [B. Beulter et al.: "Nature, 316, 552 (1985)], and since cachectin has lipoprotein lipase inhibitory activity, the administration of TNF increases the amount of triglycerides in the blood, and may possibly induce side-effects such as hyperlipemia. Elsewhere, the influence of TNF on vascular endothelial cells [J. R. Gamble et al.: J. Exp. Med., 162, 2163 (1985)], and its bone absorbing action [D. R. Beltolini et al.: Nature, 319, 516 (1986)] have been reported.

On the other hand, the recent advance in recombinant DNA technology has made it possible to substitute an amino acid in a useful protein by another amino acid, and to add an amino acid or to delete an amino acid from it. A number of research works have been conducted for modifying a naturally occurring protein and creating proteins which meet a specific purpose.

FIG. 1 accompanying this application shows the essential amino acid sequence of natural-type human TNF including a partial modification by the present inventors. The amino acid sequence of natural-type human TNF is known, e.g., see *Nature*, vol. 312, page 724, (1984). There have already been made some proposals on the modification of this human TNF protein.

With regard to the modification of natural-type human TNF having the amino acid sequence shown in FIG. 1 consisting of 157 amino acids by replacing some of its amino acids by other amino acids, the substitution of one or both of Cys$^{69}$ and Cys$^{101}$ by other amino acids such as Ser, Thr, Gly, Ala, Val, Leu, Ile, His, Tyr, Phe, Trp and Met (see PCT Application Laid-Open Specification WO86/04606 and Japanese Laid-Open Patent Publication No. 263199/1987); the substitution of Gly$^{122}$ by another amino acid such as Ala, Ile and Pro (see Japanese Laid-Open Patent Publications Nos. 263199/1987 and 93799/1988); and substitution of Ala$^{18}$ by another amino acid such as Pro, Gly, Ser, Val, Ile, Thr and Leu (see Japanese Laid-Open Patent Publication No. 87996/1988) have been reported.

With respect to the deletion of some amino acids on the N-terminus side in the amino acid sequence of the natural-type human TNF shown in FIG. 1, it has been reported that TNF in which amino acids Nos. 1 to 6 are deleted has cytotoxic activity (see Japanese Laid-Open Patent Publication No. 50923/1986); ten TNFs resulting from deleting 1 to 10 amino acids successively from amino acid residue No. 1 have cytotoxic activity, and TNFs resulting from deleting 6 to 8 amino acids have the highest specific activity (see PCT Application Laid-Open Specification WO86/02381); and TNF resulting from deleting amino acids Nos. 1 to 11 has cytotoxicity (Japanese Laid-Open Patent Publication No. 32486/1988).

However, these modified TNFs are still insufficient for use as an antitumor drug when their specific activity and antitumor activity spectra are considered, and it is difficult to use them as practical anti-tumor agents.

Experiments of the present inventors have shown that natural-type TNF has high side-effects, and in an experiment on mice sensitized with beta-D-galactosamine, about 50% of the tested animals died as a result of administering the TNF in a dose of about 0.1 microgram per mouse. In a similar test using TNF resulting from deletion of seven amino acids Nos. 1 to 7 from natural type amino acid, about 50% of the tested animals died as a result of administering this modified TNF in a dose of about 0.14 microgram per mouse.

It is an object of this invention therefore to provide a novel physiologically active polypeptide having antitumor activity.

Another object of this invention is to provide a novel polypeptide having higher antitumor activity than natural-type human TNF.

Still another object of this invention is to provide a novel physiologically active polypeptide having excellent antitumor activity with reduced side effects.

Yet another object of this invention is to provide a DNA fragment encoding the polypeptide and a plasmid containing the DNA fragment.

A further object of this invention is to provide a microorganism cell transformed with the plasmid, and a method of producing the polypeptide by cultivating the microorganism.

A still further object of this invention is to provide a pharmaceutical composition useful as an antitumor agent.

Additional objects of this invention will become apparent from the following description.

According to this invention, the objects of this invention are achieved by a novel physiological polypeptide represented by the following amino acid sequence (I)

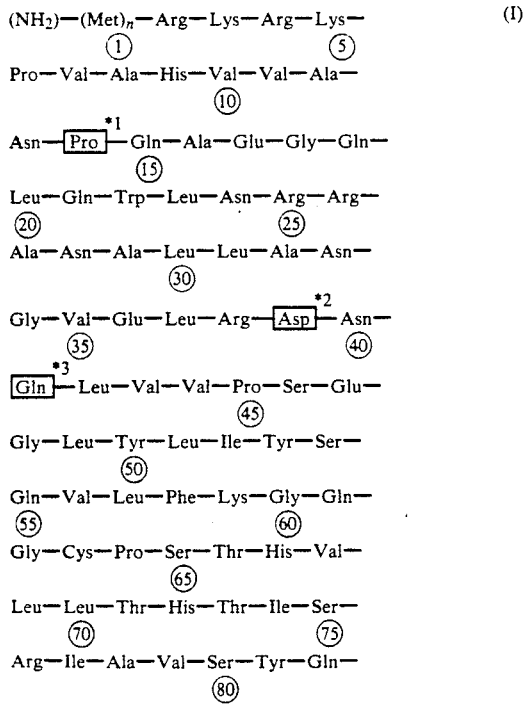

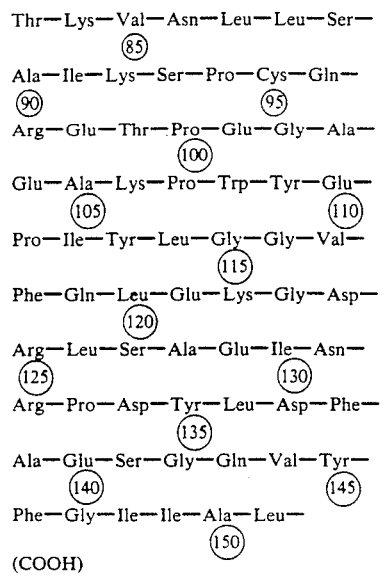

in which n represents 0 or 1, (NH$_2$) represents the amino-terminus and (COOH) represents the carboxy-terminus.

The polypeptide of this invention having the above amino acid sequence (I) is basically characterized by the fact that its amino acid sequence corresponds to the amino acid sequence of natural-type human TNF shown in FIG. 1 of the accompanying drawings in which ten amino acids Nos. 1 to 10 are deleted and (Met)$_n$-Arg-Lys-Arg is added to the amino (NH$_2$)-terminus.

The polypeptide of this invention can be used as a practical antitumor agent because it has higher antitumor activity and less side-effects, particularly lower toxicity, than the natural-type human TNF and TNF resulting from deletion of seven amino acids Nos. 1 to 7 from the N-terminus of the natural-type human TNF.

Examples given hereinbelow show that the physiologically active polypeptide of the invention represented by the amino acid sequence (I) has about 3 to 8 times as high antitumor activity as natural-type human TNF. The lethal action of the polypeptide of this invention is at least 1/20 lower than that of the natural-type human TNF, and at least about 1/10 lower than that of the above human TNF resulting from deleting seven amino acids from the N-terminus of the natural-type human TNF. Accordingly, when the antitumor activities of these polypeptides are considered from the viewpoint of specific activity and lethal action, the above experimental data mean that the polypeptide of this invention is about 160 times as advantageous as the natural-type human TNF, and about 45 times as advantageous as the human TNF resulting from deleting seven amino acids from the N-terminus of the natural-type human TNF.

Accordingly, the polypeptide of this invention has high safety for medical use in addition to its very high antitumor activity.

The polypeptide, the DNA fragment encoding it, the plasmid containing the DNA fragment, the microorganism cell containing the plasmid, the process for producing the polypeptide, and the pharmaceutical composition comprising the polypeptide provided by this invention will be described below in detail.

The polypeptide of this invention is composed of 150 or 151 amino acids represented by the above amino acid sequence (I). It should be understood that so long as the polypeptide of this invention substantially retains its antitumor activity and substantially has its low side-effects, some amino acids after the N-terminus $(H_2N)_n$-Arg-Lys-Arg may be deleted or replaced by other amino acids, or amino acids may be added.

Investigations of the present inventors have led to the determination that a polypeptide resulting from replacing at least one of Pro*1, Asp*2 and Gln*3 by His, Asn and Ser respectively and independently from each other in the amino acid sequence (I) equally has excellent antitumor activity. This modified polypeptide may be one resulting from replacing Pro*1 by His and one resulting from replacing Asp*2 and Gln*3 by Asn and Ser respectively.

The amino acid sequence (I) in accordance with this invention may, or may not, contain Met at the amino-terminus. Met is attributed to the initiation codon inserted in the plasmid when the polypeptide is produced in accordance with the present invention. Accordingly, the resulting polypeptide may exist with Met bonded to the amino-terminus.

The amino acid sequence (I) of the invention may be modified, for example, as shown below. The amino acid numbers mean the numbers indicated in the above amino acid sequence (I).

| Amino acids in the amino acid sequence (the numbers show the positions) | Substitution or deletion |
| --- | --- |
| Lys (5) | deletion |
| Val (7) | Ala |
| Val (10) | Leu |
| Val (11) | Ile |
| Ala (12) | Gly, Ile, Ser, Thr, Val, Leu or Pro |
| Ala (16) | Val |
| Gly (18) | Glu |
| Arg (25) | Asn |
| Arg (26) | His, Ala, Glu or Thr |
| Ala (27) | Asp |
| Asn (28) | Arg |
| Ala (29) | His, Met or Gln |
| Leu (30) | Phe |
| Ala (32) | Gln |
| Asn (33) | Asp |
| Val (35) | Phe |
| Glu (36) | Ser |
| Arg (38) | Ser |
| Val (43) | Leu |
| Cys (63) | Ala, Ser or Leu |
| Thr (66) —His (67) | His, Thr, Tyr, Tyr—His, His—Tyr, Tyr—Thr or Thr—Tyr |
| Leu (88) | Tyr or deletion |
| Ser (89) | deletion |
| Cys (95) | Ala, Ser or Leu |
| Gly (116) | Ala, Ile or Pro |
| Ala (27) —Val (43) | Asp—Arg—Ala—Phe—Leu—Gln—Asp—Gly—Phe—Ser—Leu—Ser—Asn—Asn—Ser—Leu—Leu |

The present invention provides a DNA fragment encoding the amino acid sequence (I) given above. The DNA fragment may be a double-stranded DNA fragment composed of a single-stranded DNA represented by the following base sequence (II)

(5')(ATG)<sub>n</sub>—CGT—AAG—CGC—
AAG—CCT—GTA—GCC—CAT—GTT—GTA—GCA—
AAC—CCT—CAA—GCT—GAG—GGG—CAG—CTC—
CAG—TGG—CTG—AAC—CGC—CGG—GCC—AAT—
GCC—CTG—CTG—GCC—AAT—GGC—GTG—GAG—
CTG—AGA—GAT—AAC—CAG—CTG—GTG—GTA—
CCA—TCA—GAG—GGC—CTG—TAC—CTC—ATC—
TAC—TCC—CAG—GTC—CTC—TTC—AAG—GGC—
CAA—GGC—TGC—CCG—TCG—ACC—CAT—GTG—
CTC—CTC—ACC—CAC—ACC—ATC—AGC—CGC—
ATC—GCC—GTC—TCC—TAC—CAG—ACC—AAG—
GTC—AAC—CTC—CTC—TCT—GCG—ATC—AAG—
AGC—CCC—TGC—CAG—AGG—GAG—ACC—CCA—
GAG—GGG—GCT—GAG—GCC—AAG—CCA—TGG—
TAT—GAG—CCC—ATC—TAT—CTG—GGA—GGG—
GTC—TTC—CAG—CTG—GAG—AAG—GGT—GAC—
CGA—CTC—AGC—GCT—GAA—ATC—AAT—CGG—
CCC—GAC—TAT—CTC—GAC—TTT—GCC—GAG—
TCT—GGG—CAG—GTC—TAC—TTT—GGG—ATT—
ATT—GCC—CTG-(3')

wherein n represents 0 or 1, 5' represents the 5'-terminus and 3' represents the 3'-terminus, and a single-stranded DNA complementary to it.

The DNA fragment (II) may also be a double-standard DNA fragment composed of a single-stranded DNA resulting from bonding the following base sequence (II')

(5')-CATCATAACGGTTCTGGCAAAT
ATTCTGAAATGAGCTGTTGACAATTAATCATC
GAACTAGTTAACTAGTACGCAAGTTCACGTAA
AAAGGGTATCGATA-(3')

to the 5'-terminus of the base sequence (II) and a single-stranded DNA complementary to it.

The base sequence (II') has the function of efficiently expressing the gene of the polypeptide of this invention.

The "DNA fragment encoding the amino acid sequence (I)" or the "double-stranded DNA fragment" in this invention does not necessarily have to contain a base sequence quite the same as the above base sequence (II) if when the plasmid contained in it is introduced into a host and the host is cultivated, the physiologically active polypeptide of the amino acid sequence (I) is expressed. For example, DNA fragments (e.g., intron) other than the structural genes may be inserted in the base sequence (II).

Vectors used for forming the plasmid containing the DNA fragment encoding the amino acid sequence (I) in this invention include, for example, vectors for *Escherichia coli*, vectors for *Bacillus subtilis*, vectors for yeasts, vectors for various cultivated animal cells, and vectors for various cultivated plant cells. The vectors for *Escherichia coli* are generally used advantageously. Examples of vectors that can be used in this invention are listed below. The parenthesized descriptions indicate the depository, the deposit number, manufacturer or the literature describing the particular vector.

(1) Vectors for *Escherichia coli* pBR322 (ATCC 31344), pBR329 (ATCC 37264), pACYC184 (ATCC 37033), pDR540 (ATCC 37282), pMB9 (ATCC 37019), pDR720 (Pharmacia), pUC9 (ATCC 37252), pUC19 (ATCC 37254), PUC13 (Pharmacia), pPL-lambda (Pharmacia), pKK223-3 (Pharmacia), pYS31N (S. Nakamura et al, J. Biotechnol., in press), and pAA41 [T. Masegi et al., Agric. Biol. Chem., 52, 1609 (1988)]. Of these, pYS31N and pAA41 are preferred.

(2) Vectors for *Bacillus subtilis* pBS7 (ATCC 37280), pC194 (ATCC 37034), and pE194 (ATCC 37128).

(3) Vectors for yeasts

YEp13 (ATCC 31125), YCp19 (ATCC 37364), YRp7 (ATCC 37060), YIp32 (ATCC 37052), and YRp17 (ATCC 37078).

(4) Vectors for cultivated animal cells pSV2-gpt (ATCC 37145), pSV2-neo (ATCC 37149), pSV2-dhfr (ATCC 37146), pSVL (Pharmacia), and pKSV-10 (Pharmacia).

(5) Vectors for cultivated plant cells

Ti plasmid.

In addition to including the DNA fragment encoding the amino acid sequence of the invention, it is possible to insert at least one gene having an expression controlling or other functions into the vectors, and this is generally preferred.

Examples of controlling and other functions to be inserted into the vectors include various promoters, for example, promoters of genes of *Escherichia coli*, such as tryptophan operon (trp), lactose operon (lac), $P_L$, tac, trc, lpp, phoA and beta-lactamase, promoters of genes derived from *Bacillus subtilis* such as chloramphenicolresistant genes, erythromycin-resistant genes, amylase, penicillinase and protease, promoters of genes derived from yeast such as galactose operon, alcohol dehydrogenase, phosphoglycerate kinase, glyceraldehydrophosphate dehydrogenase, alpha-factor, pho5 and AOXI, and promoters functioning in cultivated animal cells such as SV-40, immunoglobulin and adenovirus; an initiation codon, a termination codon and a tandem termination codon; terminaters derived from *E. coli* trp A gene and *E. coli* lpp gene; and enhancers derived from SV-40 and immunoglobulins. Of these, use of trp promoter, the initiation codon, tandem termination codon, and *E. coli* trp A gene terminater gives especially favorable results.

Any host which permits expression of the polypeptide having the amino acid sequence (I) may be used in this invention. Generally *Escherichia coli*, *Bacillus subtilis*, *Saccharomyces cervisiae*, *Zygosacharomyces pombre*, *Pichia pastaris* (K. Ogata et al., Agric. Biol. Chem., 33, 1519, 1969), and cultivated animal cells may be used in this invention. Specific examples of the hosts include *Escherichia coli* strains such as C600r-m-(ATCC 33525), HB101 (ATCC 33694), W3110 (ATCC 27325), DH1 (ATCC 33849), JA221 (ATCC 33875), JM101 (ATCC 33876), 1776 (ATCC 31244), RR1 (ATCC 31343), and LE392 (ATCC 33572); *Bacillus subtilis* strains such as Marberg 168; *Saccharomyces cervisiae* strains such as SHY3 (ATCC 44771); and animal cells such as COS-1, COS-7, L, CHO, BHK and CV-1.

Culture media suitable for cultivating the hosts are used as media for expressing the polypeptide of this invention using the transformants mentioned above. Examples of the culture media are nutrient broth, brain heart infusion and YM-broth (all of these are available from Difco Company) and L-broth, LB-broth and M9 medium described in T. Maniatis et al., ed. "Molecular Cloning", Cold Spring Harbor Laboratory (1983). Of these, the M9 medium is preferred. For stabilization of the plasmid, ampicillin is desirably added in an amount of 10 to 50 micrograms/ml to the medium.

Cultivation of the transformants is carried out by aeration cultivation by usual shaking at a temperature of 25° to 40° C., preferably about 37° C. Addition of 3-beta-indoleacrylic acid is preferred in order to induce expression.

After the cultivation, a lysate of the transformants is obtained by a general method, and the polypeptide contained in the lysate is separated and purified. The separating and purifying method is preferably gel filtration, ion exchange chromatography, chromatofocusing, affinity chromatography or combinations of these methods. Affinity chromatography using an anti-TNF antibody is especially effective.

Since the physiologically active polypeptide provided by this invention has very high antitumor activity and very little side-effects, particularly very low toxicity, it is utilized as a pharmaceutical composition for use as an antitumor agent. The pharmaceutical composition may comprise the physiologically active polypeptide as an active ingredient and an inert carrier. In using the polypeptide of this invention as an active ingredient of the pharmaceutical composition, the polypeptide may be modified by known means, for example, by modification with polyethylene glycol (PEG), dextran or poly-DL-alanine, in order to reduce the antigenicity of the polypeptide or to enhance its physiological activity.

The form of the pharmaceutical composition may be, for example, an injection composition or a suppository. For injection, it is preferably used as a composition for intravenous injection.

An injecting composition may comprise a mixture of a pharmaceutically effective amount of the polypeptide of the invention and a pharmaceutically acceptable carrier. It may also contain an excipient generally added to injection compositions, such as amino acids, carbohydrates, cellulose derivatives, polyvinyl pyrrolidone, organic acids and inorganic compounds. Specific examples include glycine, arginine, alanine and pharmaceutically acceptable salts of these as the amino acids; mannitol, inositol, xylitol, lactose and glucose as the carbohydrates; carboxymethyl cellulose sodium and methyl cellulose as the cellulose derivatives; polyvinylpyrrolidone having a molecular weight of 10,000 to 1,000,000 as the polyvinylpyrrolidone; ascorbic acid, citric acid and salts of these as the organic acids; and sodium hydrogen phosphate, sodium hydrogen carbonate and sodium acetate as the inorganic compounds.

Distilled water, physiological saline and Ringer's solution for injection may be used to dissolve the excipient.

As required, a stabilizer, a surface-active agent, an isotonizing agent, a soothing agent, an antiseptic and a buffer may be incorporated in the injecting solution. Specific examples include antioxidants such as sodium pyrosulfite and 2-ascorbic acid and chelating agents such as EDTA and thioglycol as the stabilizer; nonionic surface-active agents such as polysorbate and polyoxyethylene derivatives as the surface-active agent; sodium chloride as the isotonizing agent; benzyl alcohol, ridocaine and procaine as the soothing agent; parabens chlorobutanol, benzalconium chloride and thimerosal as the antiseptic; and sodium citrate, sodium acetate and sodium phosphate as the buffer.

The production of the polypeptide of this invention and evaluation of its activity will be described below in detail.

(A) Cloning of human TNF qene

Human TNF gene can be obtained by selecting several codons specifying the amino acids (D. Pennica et al. cited above) constituting the human TNF protein, and chemically synthesizing the human TNF protein. In designing the human TNF gene, it is desired to select codons most suited for a host cell used, and to provide sites of cleavage with suitable restriction endonucleases so as to permit easy cloning and gene modification later. Preferably, a DNA region encoding the human TNF protein has a translation initiation codon (ATG) with the reading frame coinciding with its upstream, and a translation termination codon (TGA, TAG or TAA) with the reading frame coinciding with its downstream. Preferably in order to increase the expression efficiency, two or more translation termination codons are linked in tandem. Furthermore, by using cleavage sites of endonucleases acting on its upstream and downstream sides, this human TNF gene can be cloned into a suitable vector. An example of the base sequence of this human TNF gene is shown in FIG. 1.

Desirably, the human TNF gene designed as above is produced by dividing it into a plurality of oligonucleotides as shown in FIG. 2 with respect to each of the upper and lower chains, chemically synthesizing these oligonucleotides, and then linking them with each other. Synthesis methods for the individual oligonucleotides include, for example, the diester method [H. G. Khorana, "Some Recent Developments in Chemistry of Phosphate Esters of Biological Interest", John Wiley and Sons, Inc., New York (1961)], the triester method [R. L. Letsinger et al., J. Am. Chem. Soc., 89, 4801 (1967)] and the phosphite method [M. D. Matteucci et al., Tetrahedron Lett., 21, 7190 (1980)] Synthesis by the phosphite method using an entirely automated DNA synthesizing machine is preferred from the view point of the synthesizing time, the yield and the simplicity of the operation. The synthesized oligonucleotides may be purified by, for example, gel filtration, ion exchange chromatography, gel electrophoresis, and high-performance liquid chromatography on a reverse-phase column.

The hydroxyl groups of the 5'-terminus of the synthesized oligonucleotides are phosphorylated with T4-tripolynucleotide kinase, for example. Then, the oligonucleotides are annealed, and linked with T4-DNA ligase, for example. To synthesize the human TNF gene by linking the synthetic oligonucleotides, it is preferred to divide the oligonucleotides into some blocks, linking them in each block, clone the linked oligonucleotide blocks into a vector, and then linking the DNA fragments in these blocks. pTNF1BR, pTNF2N and pTNF3 are preferably used as plasmids containing the DNA fragment blocks constituting the human TNF gene.

After the cloned DNA fragments in the blocks constituting the human TNF gene are linked, the ligated DNA fragments may be joined to the downstream end of the promoter SD sequence to produce an expression gene. Usable promoters are, for example, trp promoter, lac promoter, tac promoter, $P_L$ promoter and lpp promoter. The trp promoter is especially preferred. Preferred plasmids having trp promoter are pYS31N and pAA41. To increase the efficiency of expression, a terminater which functions efficiently in E. coli can be attached downstream of the human TNF gene. Examples of the terminater are an lpp gene terminater and a trp gene terminater. The trp A terminater is especially preferred. Preferably, pAA41 is used as a plasmid having the trp A terminater. By cloning this human TNF gene into a vector derived, for example, from pBR322, an expression plasmid can be prepared. Preferably, pTNF401NN and pTNF401A are used as a plasmid expressing the human TNF gene.

(B) Cloning of a novel polypeptide gene having antitumor activity

The resulting plasmid expressing the human TNF gene is digested with a suitable restriction endonuclease to remove a specific region of the human TNF gene and then by using synthetic oligonucleotides, the gene is repaired. This technique permits preparation of an expression plasmid containing a DNA encoding a novel antitumorally active polypeptide resulting from replacing a particular amino acid in the human TNF protein by another amino acid, deleting it, or adding another amino acid. Preferred plasmids expressing the novel anti-tumorally active polypeptide gene are, for example, pTNF471, pTNF472 and pTNF601.

(C) Determination of the expression and evaluation of the activity

E. coli, B. subtilis and yeasts are, for example, used as microorganism hosts for expressing the human TNF gene and the novel antitumorally active polypeptide genes. E. coli is especially preferred. The above plasmid expressing the human TNF gene and the plasmid expressing the novel antitumorally active polypeptide can be introduced into microorganism hosts such as E. coli C600r-m- strain by a known method [e.g., M. V. Norgard et al., Gene, 3, 279 (1978)].

The resulting recombinant microorganism cells are cultivated by methods known per se. M9 medium containing glucose and casamino acids may, for example, be used as the culture medium. As required, ampicillin, for example, is desirably added. The cultivation is carried out under conditions suitable for the recombinant microorganism, for example with aeration and stirring at 37° C. for 24 to 36 hours. At the start of, or during, the cultivation, a chemical such as 3-beta-indoleacrylic acid may be added in order to cause the promoter to function efficiently.

After the cultivation, the recombinant microorganism cells are harvested by, for example, centrifugal separation, and suspended in, for example, a phosphate buffer, and subjected to, for example, sonication to rupture the recombinant microorganism cells. Subsequent centrifugal separation gives a lysate of the recombinant microorganism cells. The protein in the lysate is separated by electrophoresis using a polyacrylamide gel containing sodium lauryl sulfate (SDS for short), and the protein in the gel is stained by a suitable method. By comparing the electrophoretic patterns using the lysate of the microorganism cells not containing the expression plasmid as a control, the expression of the human TNF gene or the novel antitumorally active polypeptide gene is determined.

The antitumor activities of the resulting human TNF protein and novel antitumorally active polypeptide are evaluated by, for example the in vivo activity measuring method by which the effect of necrotizing Meth A sarcoma transplanted in a mouse is examined (Carswell et al., cited hereinabove), or the in vitro activity measuring method by which cytotoxicity on mouse L cells is examined Ruff, J., Immunol., 126, 235 (1981)].

The separation and purification of the human TNF protein and the novel antitumorally active polypeptide from the E. coli lysates may be carried out in accordance with usually known protein separation and purification methods. One method which can be advantageously used in this invention is affinity column chromatography using antibody to the human TNF protein.

Especially preferably used is affinity column chromatography using a mouse monoclonal antibody to the human TNF protein. By using the resulting purified products of the human TNF protein and the novel antitumorally active polypeptide, in vivo antitumor activity (referred to hereinabove) and side effects can be studied.

The side effects of the human TNF protein and the novel antitumorally active polypeptide may be evaluated by, for example, an in vitro method typified by measurement of cachectin activity or an in vivo method by which these proteins are administered to experimental animals such as mice, and the lethal doses or the degree of hypoprotein is measured.

Thus, according to this invention, a novel physiologically active polypeptide different from known human TNF proteins can be obtained. By using this novel antitumorally active polypeptide, a pharmaceutical composition having excellent antitumor activity can be provided.

BRIEF DESCRIPTION OF THE ACCOMPANYING DRAWINGS

FIG. 1 shows the base sequence of a designed human TNF gene;

FIG. 2 shows the base sequences of chemically synthesized oligonucleotides;

Figure 3:
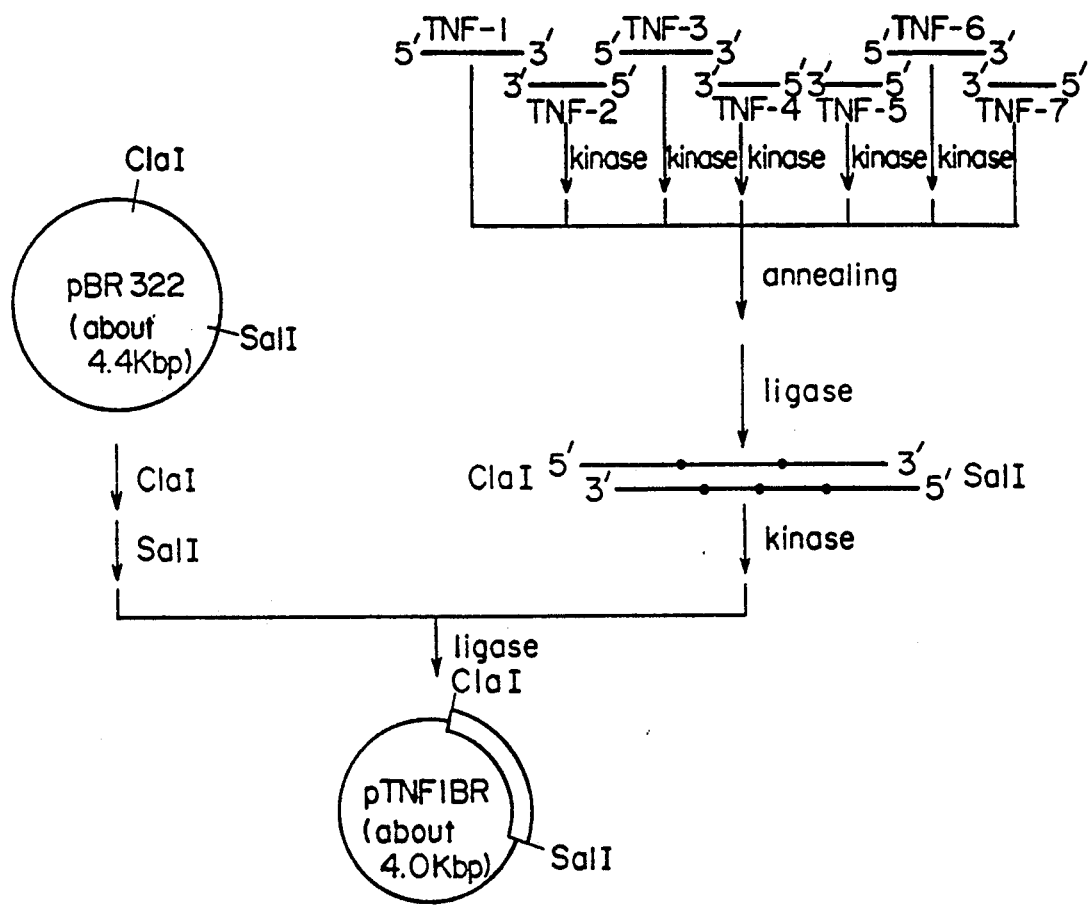
Figure 4:
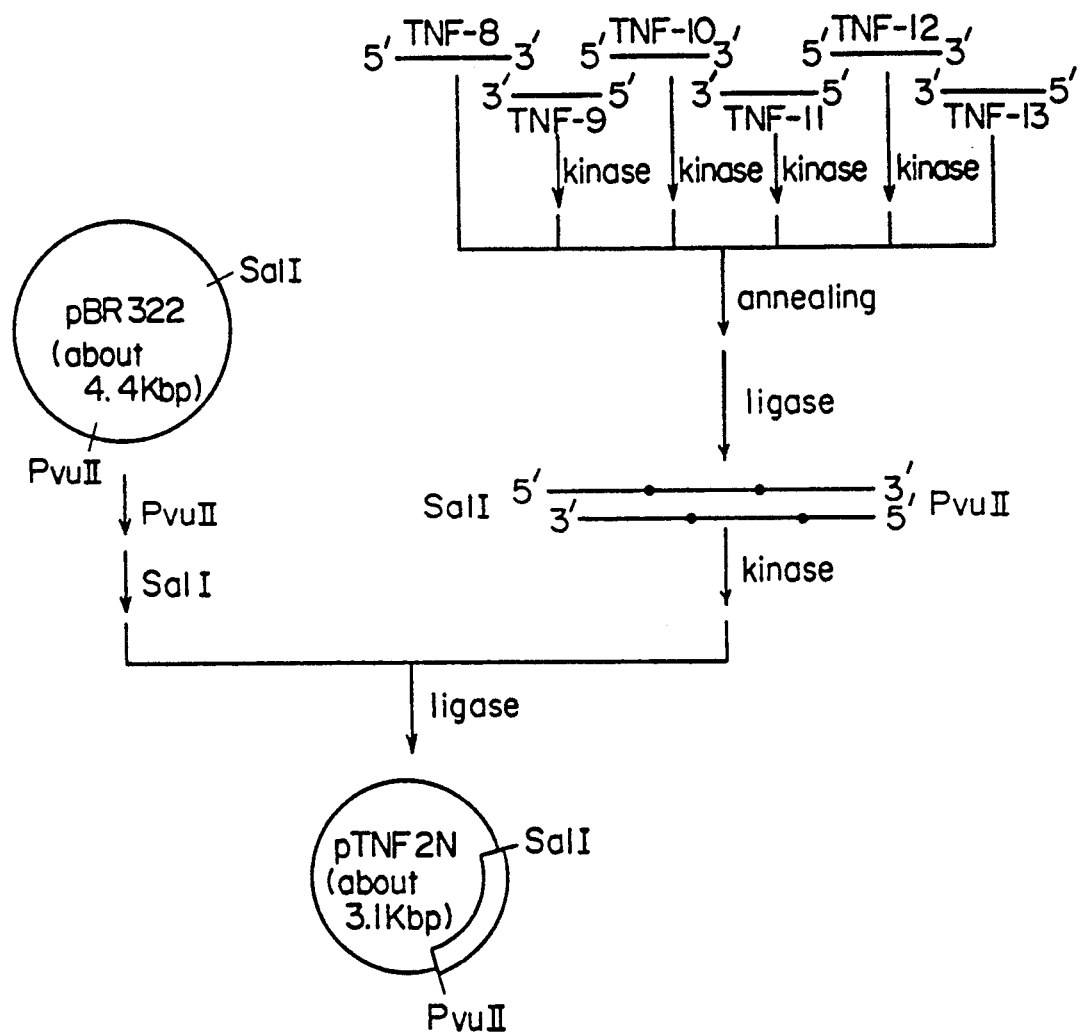
Figure 5:
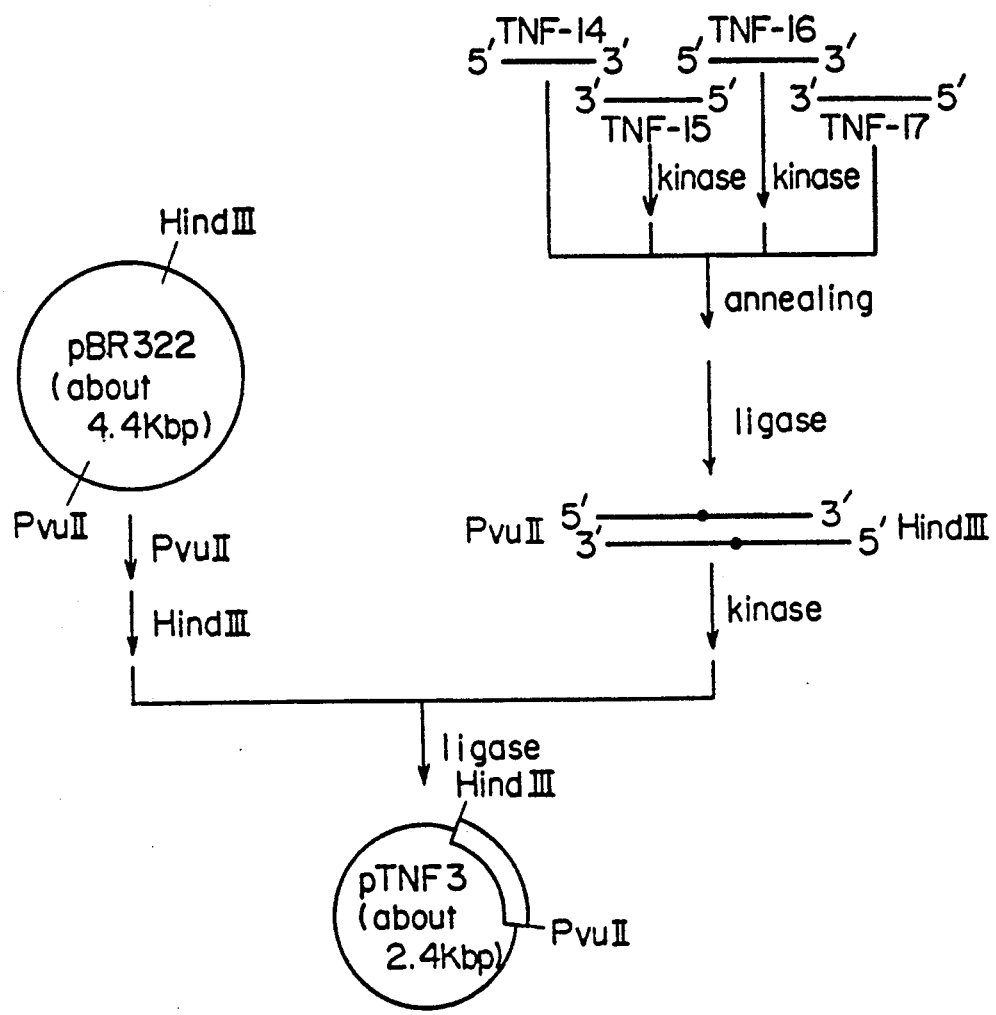
Figure 6:
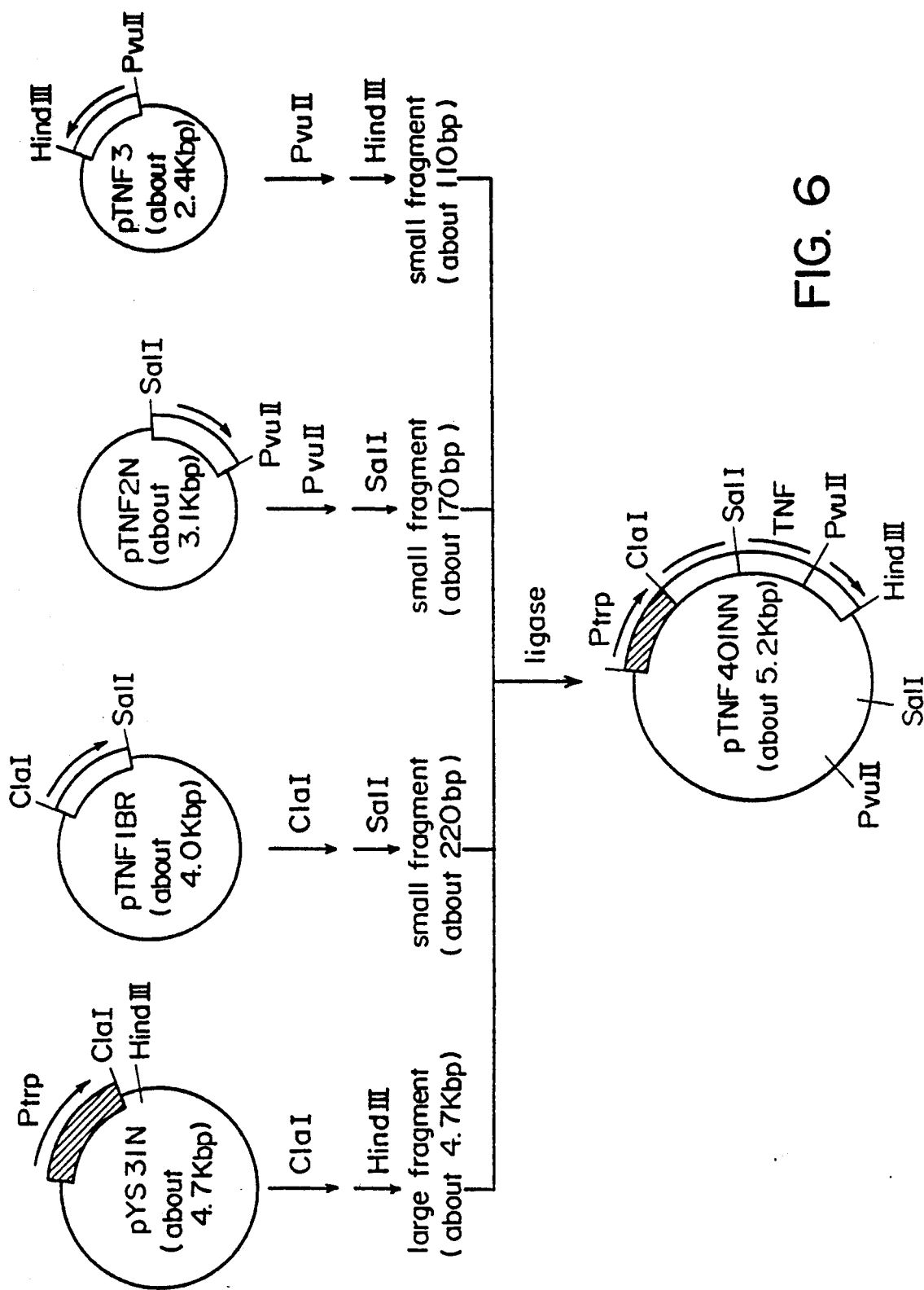
Figure 8:
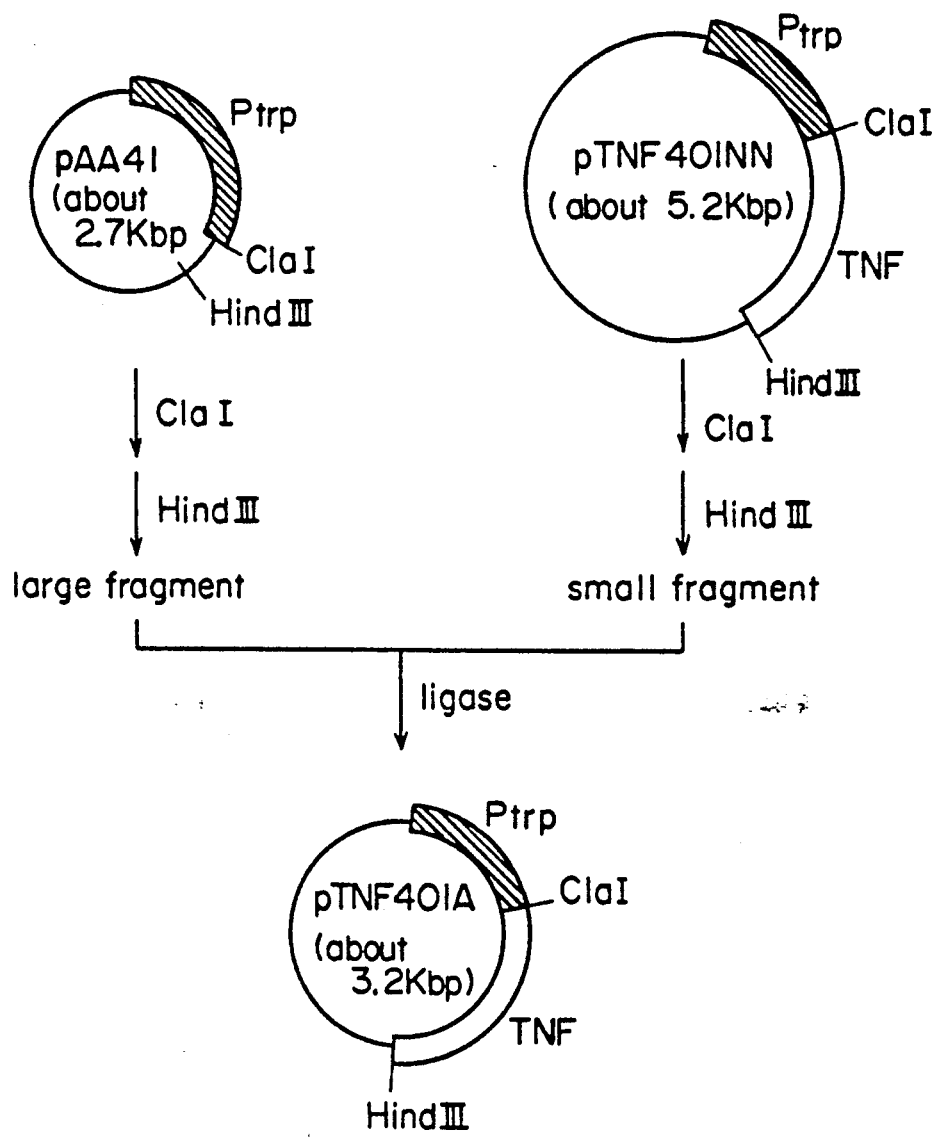
Figure 10:
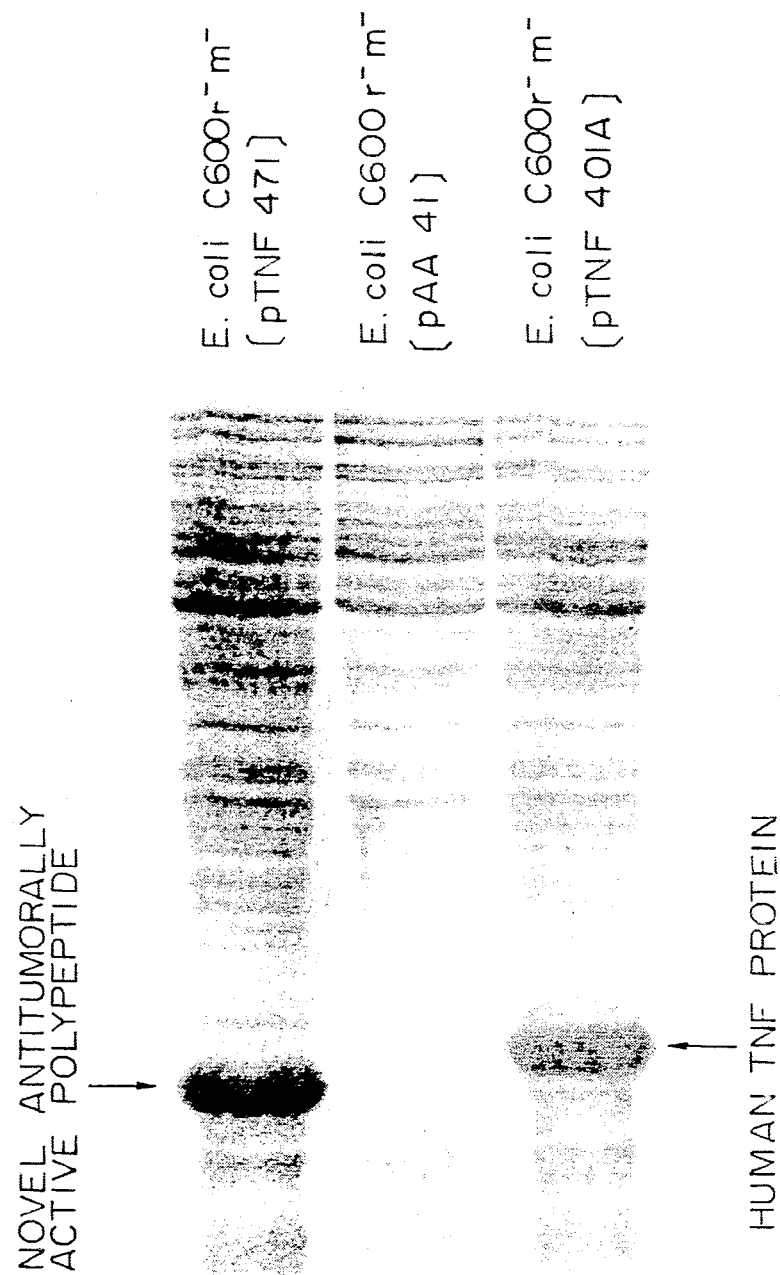
Figure 12:
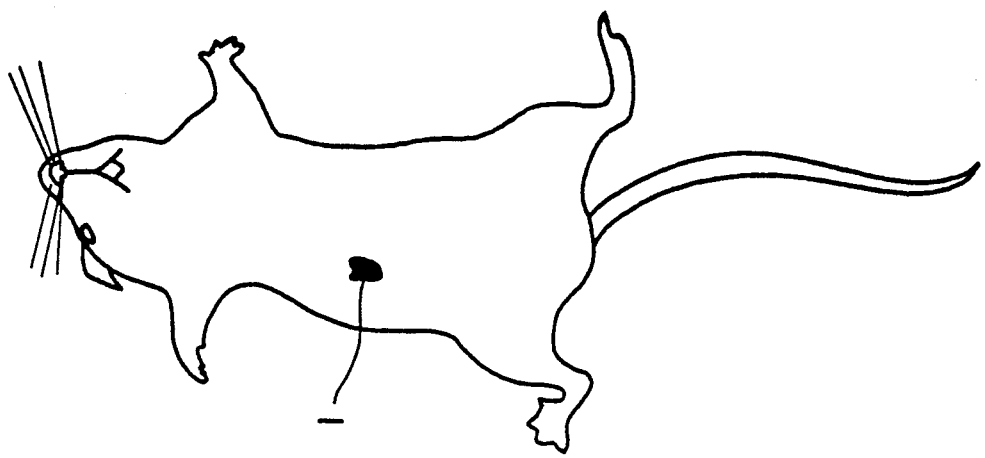
Figure 11:
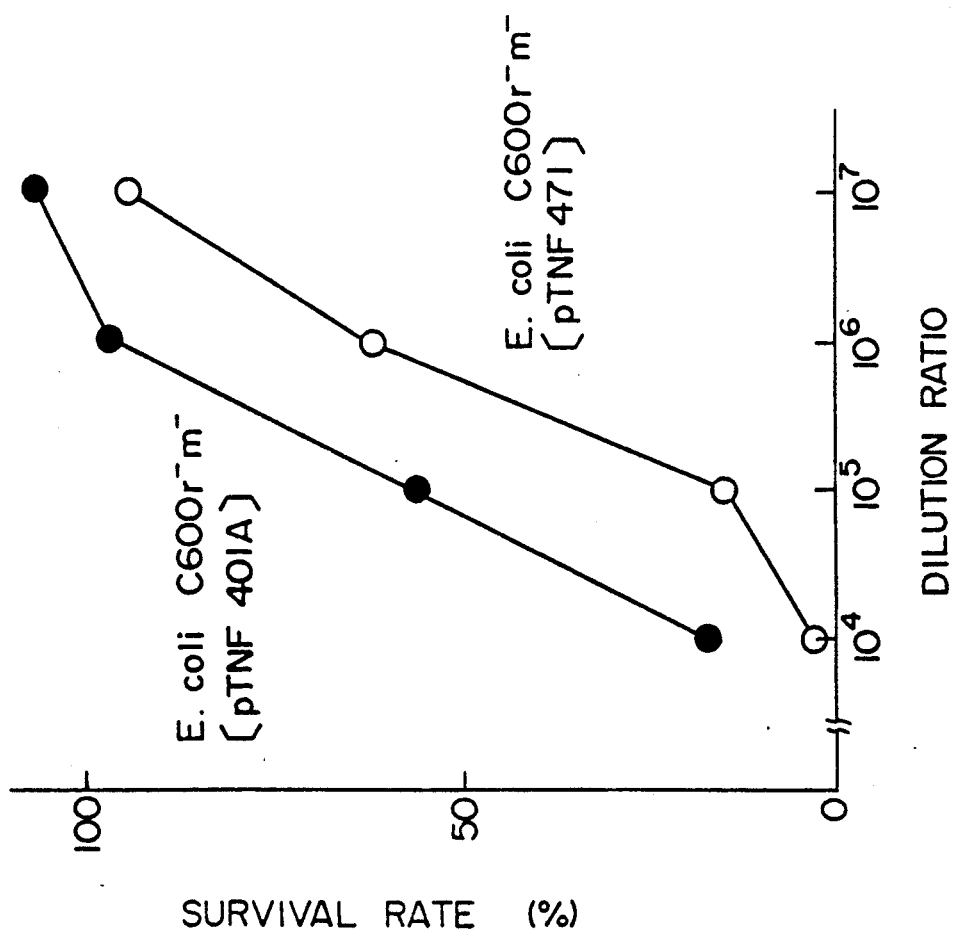
Figure 13:
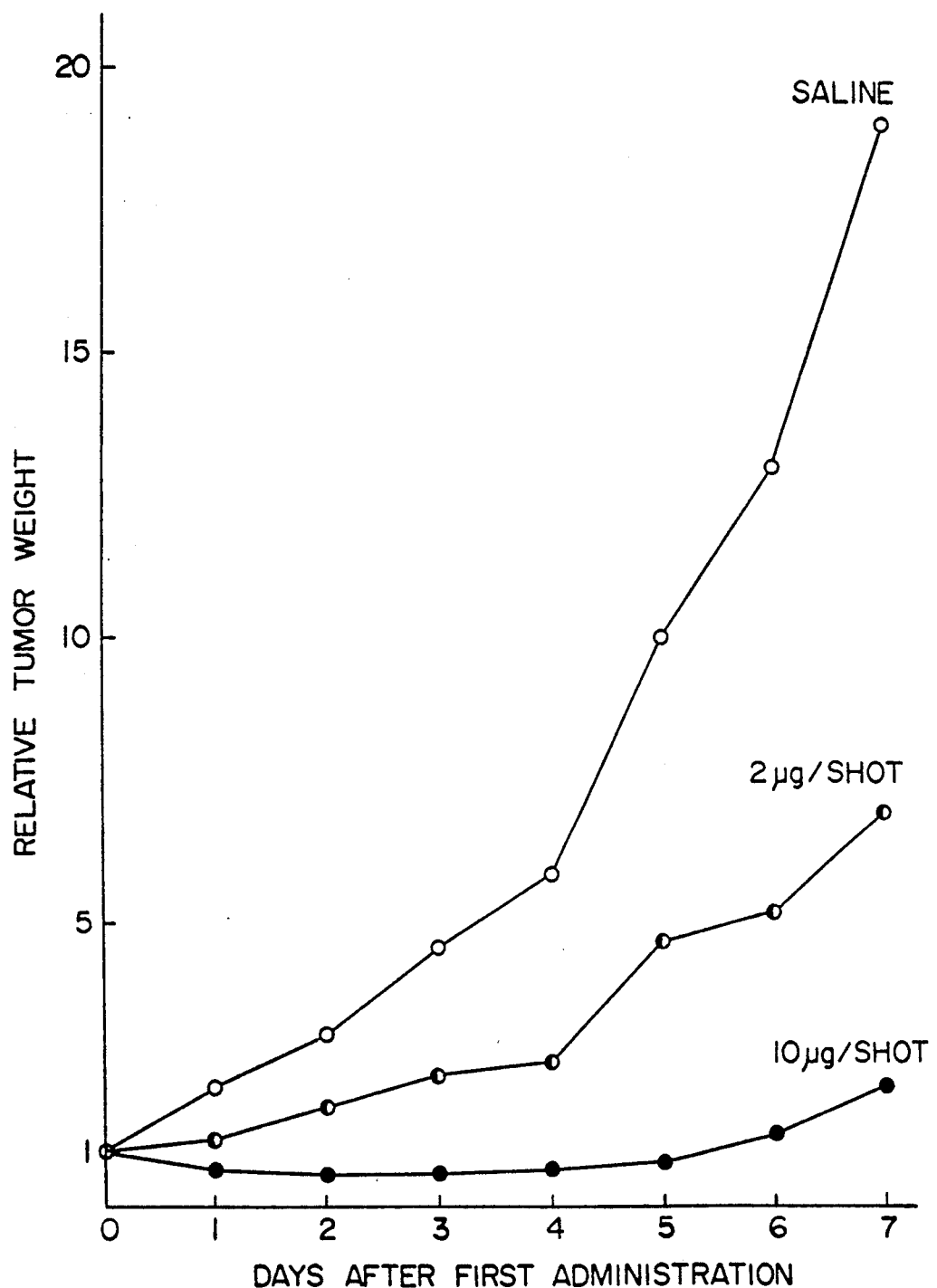
Figure 16:
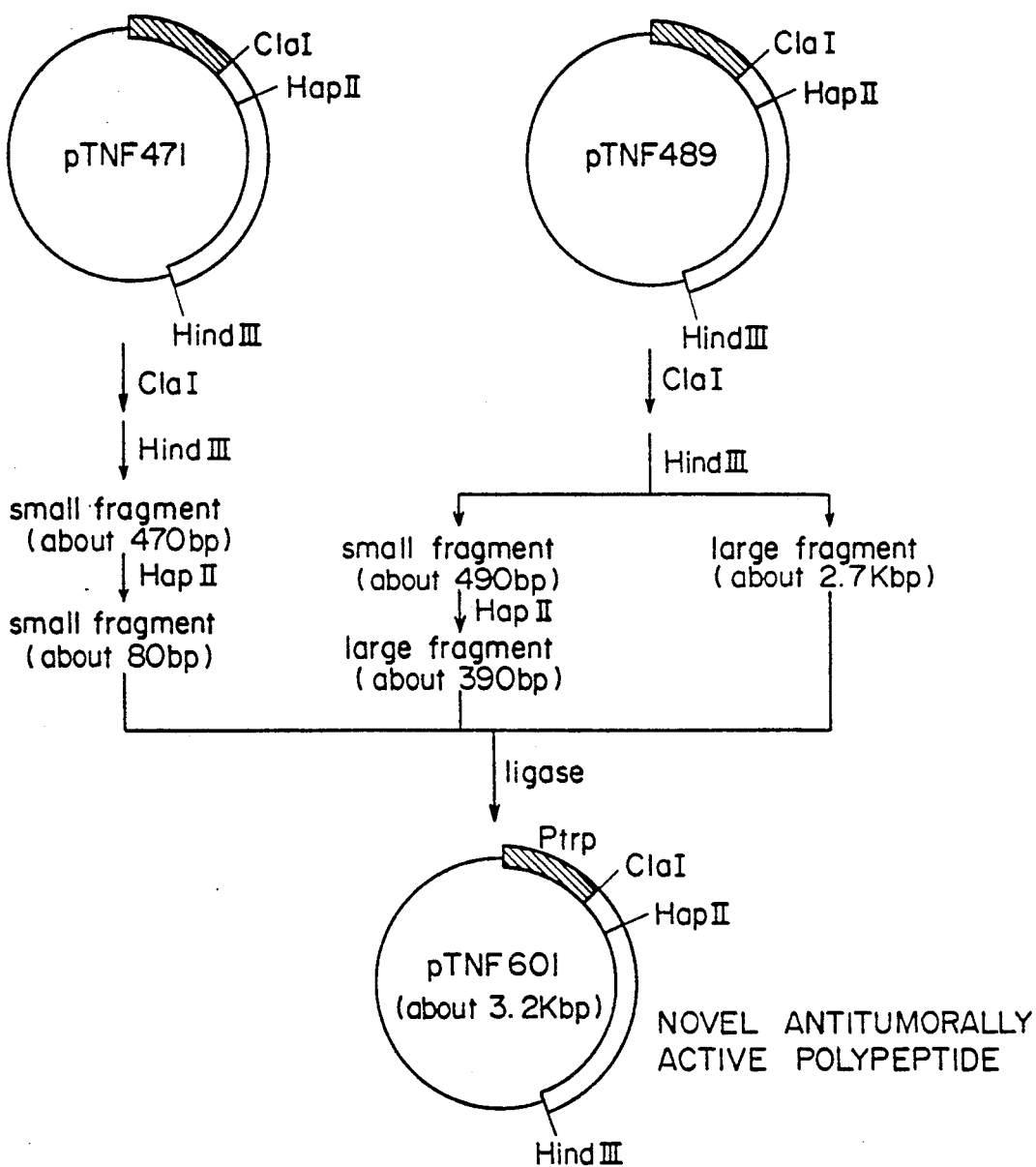

FIGS. 3, 4 and 5 respectively show methods of preparing plasmids pTNF1BR, pTNF2N and pTNF3 having part of human TNF gene;

FIG. 6 shows a method of preparing plasmid pTNF401NN capable of expressing the human TNF gene;

FIG. 7B shows a method of preparing an expression vector pAA41 from the oligonucleotides shown in FIG. 7A;

FIG. 8 shows a method of preparing a plasmid pTNF401A capable of expressing the human TNF gene;

FIG. 9B shows a method of preparing a plasmid pTNF471 from the oligonucleotides shown in FIG. 9A and capable of expressing the novel antitumorally active polypeptide gene;

FIG. 10 shows the results of determination of the expression of the human TNF gene and the novel antitumorally active polypeptide gene;

FIG. 11 shows the results of measuring the in vitro antitumor activity of the human TNF protein and the novel antitumorally active polypeptide gene;

FIG. 12 shows the results of measuring the in vivo antitumor activity of the novel antitumorally active polypeptide;

FIG. 13 shows changes with time of the relative tumor weight in a tumor-bearing mouse when the novel antitumorally active polypeptide encoded by the plasmid pTNF471 is administered to the mouse;

FIG. 14 shows the base sequences of synthetic oligonucleotides used in preparing the plasmid pTNF472 capable of expressing the novel antitumorally active polypeptide;

FIG. 15B shows a method of preparing the plasmid pTNF489 from the oligonucleotides shown in FIG. 15A and capable of expressing the novel antitumorally active polypeptide gene; and FIG. 16 shows a method of preparing the plasmid pTNF601 capable of expressing the novel antitumorally active polypeptide.

The following examples illustrate the present invention in greater detail. It should be understood however that the invention is not limited to these examples.

EXAMPLE 1

Designing of a human TNF gene:

A human TNF gene having the base sequence shown in FIG. 1 was designed. The base sequence of the structural gene portion of the human TNF precursor cDNA reported by Pennica et al. [D. Pennica et al. Nature, 312, 724 (1984)] was used as a basis. A cleavage site by a suitable restriction endonuclease was provided at a suitable position. A translation initiation codon (ATG) was attached to the 5'-side and two translation termination codons (TGA and TAA), to the 3'-side of the human TNF gene respectively. A cleavage site by restriction endonuclease ClaI was provided upstream of the 5'-side translation initiation codon to maintain a proper distance between the translation initiation codon and the SD sequence in a suitable condition to permit joining of a promoter. A site of cleavage with restriction endonuclease HindIII was provided downstream of the 3'-side termination codons to permit easy joining of a vector plasmid.

EXAMPLE 2

Chemical synthesis of oligonucleotides

The human TNF gene designed in Example 1 was divided into 17 oligonucleotides as shown in FIG. 2. These oligonucleotides were synthesized by the phosphite method using an entirely automated DNA synthesizer (Model 380A made by Applied Biosystems). The synthesized oligonucleotides were purified in accordance with the Manual of Applied Biosystems, Inc.

Specifically, an aqueous ammonia solution containing the synthetic oligonucleotides was maintained overnight at 55° C. to remove the protective groups of the DNA bases, and by gel filtration using a Sephadex G-50 fine gel (Pharmacia), high-molecular-weight synthetic oligonucleotide fractions were recovered. The oligonucleotide fractions were electrophoresed on a polyacrylamide gel containing 7M urea (gel concentration 20%), and the electrophoretic patterns were observed by the ultraviolet shadowing method. Bands having the desired size were cut out. The polyacrylamide gel fragments were crushed finely, and 2 to 5 ml of a dissolving buffer [500 mM NH$_4$OAc - 1 mM EDTA - 0.1% SDS (pH 7.5)] was added. The mixture was shaken overnight at 37° C. The aqueous layer containing the desired DNA was recovered by centrifugal separation. Finally, the solution containing the synthetic oligonucleotides was charged onto a gel filtration column (Sephadex G-50) to give purified products of the synthetic oligonucleotides. As required, the polyacrylamide gel electrophoresis was repeated to increase the purity of the synthetic oligonucleotides.

EXAMPLE 3

Cloning of chemically synthesized human TNF gene

Using the 17 synthetic oligonucleotides (TNF-1 to TNF-17) prepared in Example 2, the human TNF gene was divided into three blocks and cloned.

The 5'-terminus of 0.1 to 1.0 microgram of each of the synthetic oligonucleotides TNF-2 to TNF-6 was phosphorylated with 5 to 15 units of T4-polynucleotide kinase (*E. coli* B type, produced by Takara Shuzo Co., Ltd.). The phosphorylation reaction was carried out in 5 to 20 microliters of an aqueous solution of 50 mM Tris-HCl (pH 9.5), 10 mM MgCl$_2$, 5 mM dithiothreitol and 10 mM ATP at 37° C. for 30 minutes. After the reaction, all aqueous solutions of synthetic oligonucleotides were mixed, and extracted with phenol and ether to deactivate and remove T4-polynucleotide kinase. Newly, 0.1 to 1.0 microgram of synthetic oligonucleotides TNF-1 and TNF-7 were added to the synthetic oligonucleotide mixture obtained. The mixture was heated to 90° C. and then gradually cooled to room temperature to perform annealing. The mixture was dried under reduced pressure and dissolved in 30 microliters of an aqueous solution of 66 mM Tris-HCl (pH 7.6), 6.6 mM MgCl$_2$, 10 mM dithiothreitol and 1 mM ATP, and 300 units of T4-DNA ligase (a product of Takara Shuzo) was added. The ligating reaction was carried out at 11° C. for 15 hours. After the reaction, the reaction mixture was electrophoresed on a polyacrylamide gel (gel concentration 5%), and the electrophoretic patterns were observed by the ethidium bromide staining method. Bands having the desired size (about 220 bp) were cut out, and by the method of Example 2, DNA was recovered from the polyacrylamide gel.

In the meantime, 3 micrograms of plasmid pBR 322 (about 4.4 kbp) for *E. coli* was dissolved in 30 microliters of an aqueous solution containing 10 mM Tris-HCl (pH 7.5), 60 mM NaCl and 7 mM MgCl$_2$. Ten units of restriction endonuclease ClaI (a product of New England Bio-Rad) was added, and the digestion reaction was carried out at 37° C. for 1 hour. After the digestion, the reaction mixture was extracted with phenol and then ether, and precipitated from ethanol to recover DNA. The DNA was dissolved in 30 microliters of an aqueous solution containing 50 mM Tris-HCl (pH 7.4), 100 mM NaCl and 10 mM MgSO$_4$, and 10 units of restriction enzyme SalI (a product of Takara Shuzo), and the digestion reaction was carried out at 37° C. for 1 hour. After the reaction, the reaction mixture was electrophoresed on an agarose gel (gel concentration 0.8%), and the cleavage patterns were observed by the ethidium bromide staining method. A band corresponding to a DNA portion having a size of 3.7 kbp and containing most of the plasmid pBR 322 was cut out, and the agarose gel slice was dissolved in 3 times its amount (vol/wet) of an 8M aqueous solution of NaClO$_4$. A DNA fragment (ClaI - SalI) having a size of about 3.7 kbp was recovered from the agarose gel by the glass filter method of Chen et al. [C. W. Chen et al. Anal, Biochem., 101, 3339 (1980)].

The terminals of the DNA fragment having a size of about 220 bp and containing part of the human TNF gene, which has been obtained previously, was phosphorylated in accordance with the method described hereinabove, and the product was mixed with an aqueous solution of DNA having a size of about 3.7 kbp and containing most of the plasmid pBR 322. After precipitation from ethanol, the two DNA fragments were ligated by the method described above.

Transformation of *E. coli* C600r-m- strain was carried out by an improved method of the ordinary CaCl$_2$ method (the method of M. V. Norgard et al.). Specifically, a culture medium in which *E. coli* C600r-m- strain had been cultivated for 18 hours was inoculated in 5 ml of L medium (1% tryptone, 0.5% yeast extract, 0.5% NaCl, pH 7.2), and grown until the turbidity at 600 nm (OD$_{600}$) of the culture liquid containing the cells reached 0.3. The cells were washed twice in a cold magnesium buffer (0.1M NaCl, 5 mM MgCl$_2$, 5 mM Tris-HCl (pH 7.0, 0° C.)), re-suspended in 2 ml of a cold calcium buffer [100 mM CaCl$_2$, 250 mM KCl, 5 mM MgCl$_2$, 5 mM Tris-HCl (pH 7.6, 0° C.)], and left to stand at 0° C. for 25 minutes. The cells were concentrated to 1/10 of this volume in the calcium buffer, and mixed with the aqueous DNA solution after the ligation in a ratio of 2:1 (vol:vol). The mixture was maintained at 0° C. for 60 minutes, add 1 ml of LBG medium (1% tryptone, 0.5% yeast extract, 1% NaCl, 0.08% glucose, pH 7.2), and cultivated with shaking at 37° C. for 1 hour. The culture broth was inoculated in selective media [L-basal plates containing 30 micrograms/ml of ampicillin (Sigma)] at a rate of 100 microliters/plate. The plates were cultivated at 37° C. overnight to grow the transformants. DNA was prepared from the resulting ampicillin-resistant colonies by a known method. By agarose gel electrophoresis, the production of the desired plasmid pTNF1BR (about 4.0 kbp) was determined. FIG. 3 shows the method of preparing the plasmid pTNF1BR.

By the same procedure as above, plasmid pTNF2N (about 3.1 kbp) was prepared by using synthetic oligonucleotides TNF-8 to TNF-13, and plasmid pTNF3 (about 2.4 kbp) by using synthetic oligonucleotides TNF-14 to TNF-17. FIGS. 4 and 5 show methods of preparing the plasmids pTNF2N and pTNF3.

It was determined by the method of Maxam and Gilbert [A. M. Maxam et al.: Methods in Enzymol., 65, 499 (1980)] that the synthetic oligonucleotide portions of the plasmids pTNF1BR, pTNF2N and pTNF3 containing part of the human TNF gene obtained as above had the base sequences exactly as designed.

EXAMPLE 4

Ten micrograms of the plasmid pTNF1BR obtained in Example 3 was digested with restriction endonucleases ClaI and SalI as in Example 3. The digestion product was electrophoresed on a polyacrylamide gel (gel concentration 5%). Then, in accordance with the method of Example 2, a DNA fragment (ClaI - SalI) having a size of about 220 bp and containing part of the human TNF gene was recovered from the polyacrylamide gel.

Then, 10 micrograms of the plasmid pTNF2 obtained in Example 3 was dissolved in 10 microliters of an aqueous solution containing 10 mM Tris-HCl (pH 7.5), 60 mM NaCl, and 7 mM MgCl$_2$, and 40 units of restriction endonuclease PvuII (a product of Takara Shuzo) was added. The digestion reaction was carried out at 37° C. for 1 hour. Then, in accordance with the method of Example 3, digestion with restriction endonuclease SalI and polyacrylamide gel electrophoresis (gel concentration 5%) were carried out. Thereafter, in accordance with the method of Example 2, a DNA fragment (SalI - PvuII) having a size of about 170 bp and containing part of the human TNF gene was recovered from the polyacrylamide gel.

Ten micrograms of the plasmid pTNF3 obtained in Example 3 was dissolved in 100 microliters of an aqueous solution containing 10 mM Tris-HCl (pH 7.5), 60 mM NaCl, and 7 mM MgCl$_2$, and 40 units of restriction endonuclease PvuII and 40 units of restriction endonuclease HindIII (a product of Takara Shuzo) were added, and the digestion reaction was carried out at 37° C. for 1 hour. After polyacrylamide gel electrophoresis (gel concentration 5%), a DNA fragment (PvuII - HindIII) having a size of about 110 bp and containing part of the human TNF gene was recovered from the polyacrylamide gel in accordance with the method of Example 2.

On the other hand, 5 micrograms of the plasmid pYS31N (about 4.7 kbp) containing *E. coli* trp promoter was digested as above with restriction endonucleases ClaI and HindIII. After agarose gel electrophoresis (gel concentration 0.8%), a DNA fragment (ClaI - HindIII) having a size of about 4.7 kbp and containing most of the plasmid pYS31N was recovered from the agarose gel.

The resulting three DNA fragments having a size of about 220 bp, about 170 bp and about 110 bp and containing part of the human TNF gene which were obtained as above were mixed with the DNA fragment (about 4.7 kbp) containing most of the plasmid pYS31N. After precipitation with ethanol, the mixture was subjected to ligating reaction with T4-DNA ligase. After the reaction, in accordance with the method of Example 3 the ligation product was introduced into *E. coli* C600r-m- strain, and from the transformants, clones having the desired plasmid pTNF401NN (about 6.2 kbp) capable of expressing the human TNF gene were selected. FIG. 6 shows a method of preparing the plasmid pTNF401NN.

Five micrograms of the plasmid pYS31N was partially digested with restriction endonuclease PvuII and then digested with restriction endonuclease HindIII. The digestion product was electrophoresed on an agarose gel (gel concentration 0.8%), and in accordance with the method of Example 3, a DNA fragment PvuII (2) - HindIII] having a size of about 2.7 kbp and containing trp promoter was recovered from the agarose gel.

Oligonucleotides having the base sequence shown in FIG. 7-A were synthesized and purified in accordance with the method of Example 2. The terminal of 0.5 microgram of each of the resulting two synthetic oligonucleotides was phosphorylated in accordance with the method of Example 3. After annealing, the synthetic oligonucleotides were mixed with the DNA fragment PvuII (2)-HindIII] having a size of about 2.7 kbp obtained previously. After precipitation with ethanol, the mixture was subjected to a ligation reaction with T4-DNA ligase. After the reaction, the ligation product was introduced into *E. coli* C600r-m- strain in accordance with the method of Example 3. Clones having the desired plasmid pAA41 (about 2.7 kbp) were selected from the transformants. This plasmid is a high copy high efficient expression vector resulting from removing the copy number control region from the plasmid pYS31N and joining *E. coli* trp A terminater to the downstream of the cloning site existing downstream of trp promoter. The method of its preparation is shown in FIG. 7-B.

Two micrograms of the plasmid pAA41 was digested with restriction endonucleases ClaI and HindIII in the same way as above, and after agarose gel electrophoresis (gel concentration 0.8%), a DNA fragment (ClaI - HindIII) having a size of about 2.7 kbp and containing most of the pAA41 was recovered from the agarose gel.

Furthermore, 5 micrograms of the plasmid pTNF401NN capable of expressing the human TNF gene, which had been obtained as above, was digested with restriction endonucleases ClaI and HindIII in the same way as above. After polyacrylamide gel electrophoresis (gel concentration 5%), a DNA fragment (ClaI - HindIII) having a size of about 490 bp and containing the entire region of the human TNF gene was recovered from the polyacrylamide gel in accordance with the method of Example 2.

The DNA fragment (about 2.7 kbp) containing most of the plasmid pAA41 and the DNA fragment (about 490 bp) containing the entire region of the human TNF gene obtained above were mixed, and after precipitation with ethanol, subjected to a ligating reaction with T4-DNA ligase in accordance with the method of Example 3. After the reaction, the ligation product was introduced into *E. coli* C600r-m- strain, clones having the desired plasmid pTNF401A (about 3.2 kbp) were selected from the transformants, in accordance with the method of Example 3. This plasmid has the ability to express the human TNF gene with good efficiency, and FIG. 8 shows a method of its preparation.

EXAMPLE 5

Preparation of a Plasmid Capable of Expressing the Novel Antitumorally Active Polypeptide Twenty micrograms of the plasmid pTNF401A capable of expressing the human TNF gene obtained in Example 4 was digested with restriction endonucleases ClaI and HindIII in accordance with the method of Example 4. The digestion product was subjected to polyacrylamide gel electrophoresis (gel concentration 5%) and agarose gel electrophoresis (gel concentration 0.8%). The resulting two DNA fragments (about 490 bp and about 2.7 kbp; both ClaI - HindIII) were recovered from the gels.

The DNA fragment (about 490 bp) containing the entire region of the human TNF gene was dissolved in 50 microliters of an aqueous solution containing 10 mM Tris-HCl (pH 7.4), 1C mM MgSO4 and 1 mM dithiothreitol, and 10 units of restriction endonuclease HapII (a product of Takara Shuzo) was added. The digestion reaction was carried out at 37° C. for 1 hour. After the reaction, the reaction mixture was electrophoresed on a polyacrylamide gel (gel concentration 5%), and in accordance with the method of Example 2, a DNA fragment (HapII - HindIII) having a size of about 390 bp and containing most of the human TNF gene was recovered from the polyacrylamide gel.

Oligonucleotides having the base sequences shown in FIG. 9 were synthesized and purified in accordance with the method of Example 4. The terminals of the resulting four synthetic oligonucleotides in an amount of 0.5 microgram each were phosphorylated by the method of of Example 3, and after annealing, they were ligated by using T4-DNA ligase.

After the reaction, the resulting double-stranded oligonucleotide was mixed with the DNA fragment (ClaI - HindIII) having a size of about 2.7 kbp and the DNA fragment (HapII - HindIII) having a size of about 390 bp which were obtained above, and after precipitation with ethanol, the mixture was subjected to ligation with T4-DNA ligase in accordance with the method of Example 3. After the reaction, the ligation product was introduced into *E. coli* C600r-m- strain in accordance with the method of Example 3, and clones having the desired plasmid pTNF471 (about 3.2 kbp) were selected from the transformants. This plasmid is a plasmid encoding the novel antitumorally active polypeptide represented by the amino acid sequence (I) given hereinabove. FIG. 9 shows a method of its preparation.

EXAMPLE 6

Determination of Expression

E. coli C600r-m- strain having each of the expression vector pAA41 and human TNF gene expressing plasmids pTNF401NN and pTNF401A, which were obtained in Example 4, pTNF416 [the plasmid expressing human TNF with seven amino acids at the N-terminus amino acid deleted (to be referred to as the N-terminus deleted human TNF) described in Japanese Laid-Open Patent Publication No. 248498/1987

```
(H2N)—Pro Ser Asp Lys Pro
Val  Ala  His  Val  Val  Ala  Asn
Pro  Gln  Ala  Glu  Gly  Gln  Leu
Gln  Trp  Leu  Asn  Arg  Arg  Ala
Asn  Ala  Leu  Leu  Ala  Asn  Gly
Val  Glu  Leu  Arg  Asp  Asn  Gln
Leu  Val  Val  Pro  Ser  Glu  Gly
Leu  Tyr  Leu  Ile  Tyr  Ser  Gln
Val  Leu  Phe  Lys  Gly  Gln  Gly
Cys  Pro  Ser  Thr  His  Val  Leu
Leu  Thr  His  Thr  Ile  Ser  Arg
Ile  Ala  Val  Ser  Tyr  Gln  Thr
Lys  Val  Asn  Leu  Leu  Ser  Ala
Ile  Lys  Ser  Pro  Cys  Gln  Arg
Glu  Thr  Pro  Glu  Gly  Ala  Glu
Ala  Lys  Pro  Trp  Tyr  Glu  Pro
Ile  Tyr  Leu  Gly  Gly  Val  Phe
Gln  Leu  Glu  Lys  Gly  Asp  Arg
Leu  Ser  Ala  Glu  Ile  Asn  Arg
Pro  Asp  Tyr  Leu  Asp  Phe  Ala
Glu  Ser  Gly  Gln  Val  Tyr  Phe
Gly  Ile  Ile  Ala  Leu—(COOH)
```

], or the plasmid pTNF471 expressing the novel antitumorally active polypeptide gene obtained in Example 5 was inoculated in 250 ml of M9 medium containing 30 to 50 microgrms/ml of ampicillin, 0.2% of glucose and 4 mg/ml of casamino acid [an aqueous solution (pH 7.4) of 0.6% $Na_2HPO_4$-0.3% $KH_2PO_4$-0.05% NaCl-0.1% $NH_4Cl$ was sterilized in an autoclave, and an aqueous solution of $MgSO_4$ and an aqueous solution of $CaCl_2$, which had been separately sterilized in an autoclave were added so that their final concentrations became 2 mM and 0.1 mM respectively], and cultivated at 37° C. until the $OD_{600}$ of the culture reached 0.7. Then, 3-beta-indoleacrylic acid having a final concentration of 50 micrograms/ml was addd to the culture broth, and the cultivation was continued further with shaking at 37° C. for 12 hours.

The E. coli cells were harvested by centrifugal separation, and washed with a PBS buffer (20 mM phosphate buffer containing 150 mM NaCl, pH 7.4). The washed cells were suspended in 10 ml of PBS buffer, and ruptured by using an ultrasonic generator (Model 200M, Kubota), and then the solid residues were removed by centrifugal separation.

Tris-HCl buffer (pH 6.8) SDS, 2-mercaptoethanol and glycerol were added to a portion of the resulting E. coli lysate so as to provide a final concentration of 60 mM, 2%, 4% and 10%, respectively, and SDS-polyacrylamide gel electrophoresis was performed [Suzuki, Iden (Genetics), 31, 43 (1977)]. The concentration of the separating gel was adjusted to 12.5%, and an SDS, Tris-glycine system [U. K. Laemmli, Nature, 227, 680 (1970)] was used as an electrophoretic buffer. After the electrophoresis, the proteins in the gel were stained with Coumassie Brilliant Blue R-250 (Bio-Rad), and the expression of the human TNF gene and the novel antitumorally active polypeptide gene was determined. Some of the results were copied and shown in FIG. 10.

The stained gel was subjected to a chromatoscanner (Model CS-930, Shimadzu), and the proportion of the produced human TNF protein or the novel antitumorally active polypeptide in the E. coli cytoplasmic protein was calculated. It was found that in the E. coli having the human TNF gene expressing plasmid pTNF401A, about 11%, based on the total weight of the E. coli cytoplasmic protein, of the human TNF protein was produced, and in E. coli having the plasmid pTNF471 capable of expressing the novel antitumorally active polypeptide gene, about 17%, based on the total amount of the cytoplasmic protein, of the novel antitumorally active polypeptide was produced. The amount of the human TNF protein in E. coli having the human TNF gene expressing plasmid pTNF401NN was only about 40% of that produced in E. coli containing pTNF401A, and this shows the usefulness of the expression vector pAA41.

EXAMPLE 7

Evaluation of In Vitro Antitumor Activity

The in vitro antitumor activity of the novel antitumorally active polypeptide was measured in accordance with the method of Ruff et al. cited hereinabove.

Specifically, the E. coli lysate containing the novel antitumorally active polypeptide obtained in Example 6 was diluted successively with a medium [Eagle's minimum essential medium (produced by Nissui Seiyaku) containing 5% (vol/vol) bovine fetal serum). The resulting sample (100 microliters) and 100 microliters of a suspension of mouse L-929 fibroblast cells (ATCC CCL-929) were mixed in a 96-well tissue-culture microtiter plate (Coaster). At this time, actinomycin D (Cosmegen, Banyu Pharmaceutical Co., Ltd.) was added to a final concentration of 1 microgram/ml. The microtiter plate was cultivated at 37° C. for 18 to 20 hours in air containing 5% carbon dioxide gas. Then, the living cells were stained with a crystal violet solution [prepared by dissolving 0.5% (wt/vol) of crystal violet in a 5% (vol/vol) aqueous solution of methanol. The excess of the crystal violet solution was washed off, and the microtiter plate was dried. The remaining crystal violet was extracted with 100 microliters of a 0.5% aqueous solution of SDS, and the absorbance of the extract at 595 nm was measured by an ELISA analyzer (model ETY-96, Toyo Sokki). This absorbance is proportional to the number of surviving cells. The dilution ratio of the E. coli lysate containing the human TNF protein or the novel antitumorally active polypeptide, which corresponds to 50% of the absorbance of the E. coli lysate to which no diluting solution was added, was determined from a graph (for example, FIG. 11), and this dilution ratio is defined as one unit. It is clear from FIG. 11 that 100 microliters of the E. coli lysate containing the human TNF protein encoded by the expression plasmid pTNF401A has an activity of about $1.5 \times 10^5$ units, and 100 microliters of the E. coli lysate containing the novel antitumorally active polypeptide encoded by the expression plasmid pTNF471 has an activity of about $1.2 \times 10^6$ units.

The total amount of proteins contained in the E. coli lysate containing the human TNF protein encoded by the expression plasmid pTNF401A or the novel antitumorally active polypeptide encoded by the expression plasmid pTNF471 obtained in Example 6 was determined by using a protein assay kit (made by Bio-Rad), and calculated from a calibration curve prepared by using a bovine serum albumin. From the amounts of expression, the activity values and the amounts of proteins determined above, the specific activities of the human TNF protein and the novel antitumorally active polypeptide were calculated, and the results are shown in Table 1. Table 1 shows that the novel antitumorally active polypeptide has about 64 times as high a specific activity as the human TNF protein.

TABLE 1

| Physiologically active polypeptide | Human TNF protein | Novel antitumorally active polypeptide |
|---|---|---|
| Plasmid | pTNF401A | pTNF471 |
| $\frac{\text{Physiologically active polypeptide}}{\text{Total cytoplasmic proteins in } E.\ coli}$ (%) | 11 | 17 |
| Activity (unit/100 microliters-lysate) | $1.5 \times 10^5$ | $1.2 \times 10^6$ |
| Concentration of total cytoplasmic proteins in E. coli (mg/ml-lysate) | 5.5 | 5.8 |
| Specific activity (unit/mg-physiologically active polypeptide) | $2.5 \times 10^6$ | $1.6 \times 10^7$ |

EXAMPLE 8

Separation and Purification of the Human TNF Protein, N-terminus Deleted Human TNF Protein and Novel Antitumorally Active Polypeptide Purification of the human TNF protein from the lysate obtained in Example 6 was carried out by DEAE-Sepharose column chromatography in accordance with the method of Shirai et al. [T. Shirai et al., Nature, 313, 830 (1985)]. The resulting coarsely purified product contained about 30% of the human TNF protein.

A mouse hybridoma capable of producing a monoclonal antibody against the human TNF protein was produced by the method of Koehler and Milstein [Koehler and Milstein, Nature, 256, 495 (1975)]. Specifically, male Balb/c mice were immunized with the above coarsely purified human TNF protein. The spleen cells of the immunized mice were fused with mouse myeloma cells P3-X63-Ag8-U1 [E. E. Yelton et al., Current Topics in Microbiology and Immunology, 81, 1 (1978)]. The fused cell mixture after fusion was cultivated in a selective medium to select only hybridoma cells. By examining the ability of the antibody in the culture supernatant to bind to the coarsely purified human TNF protein, clones producing an antibody to the human TNF protein were obtained.

Purification of the monoclonal antibody from the culture supernatant of the mouse hybridoma capable of producing the monoclonal antibody to the human TNF protein was carried out by using protein A Sepharose column chromatography (Pharmacia). The resulting purified monoclonal antibody was coupled with an active-type affinity support Affigel 10 (Bio-Rad) in 0.1M MOPS buffer (pH 7.5, Nakarai Chemicals) at 4° C. for 2 hours to prepare an affinity column for purification of the human TNF protein (natural-type), the N-terminus deleted human TNF protein (resulting from the deletion of 7 amino acids) and the novel antitumorally active polypeptide.

The lysate containing the human TNF protein, N-terminus deleted human TNF protein or novel antitumorally active polypeptide obtained in Example 6 was charged onto the affinity column to permit specific adsorption of only the human TNF protein, the N-terminus deleted human TNF protein or the novel antitumorally active polypeptide on the column. The column was fully washed with PBS buffer [20 mM phosphate buffer (pH 7.4), 140 mM NaCl] and 20 mM phosphate buffer (pH 7.4) containing 500 mM NaCl, and then eluted with 0.1M citrate buffer (pH 3.0) to obtain the human TNF protein, the N-terminus deleted human TNF protein or the novel antitumorally active polypeptide. The eluate was concentrated by ultrafiltration, added to PBS buffer, and electrophoresed on an SDS-polyacrylamide gel (gel cocentration 15%). After electrophoresis, protein bands in the gel were stained with a dye. One band was observed only at a position corresponding to a molecular weight of about 15,000 to 17,000. It could thus be confirmed that the human TNF protein, N-terminus deleted human TNF protein and the novel antitumorally active polypeptide having a purity of more than 98% were obtained.

The side-effects of the purified human TNF protein, N-terminus deleted human TNF protein and novel antitumorally active polypeptide obtained in this example were evaluated in terms of lethal action on mice. Specifically, 500 microliters of physiological saline containing a predetermined amount of the human TNF protein, the N-terminus deleted human TNF protein or the novel antitumorally active polypeptide and 18 mg of beta-D-galactosamine was intraperitoneally administered to 6-8 weeks old female C3H/HeJ mice (Clea Japan, Inc.), and after the lapse of 24 hours, the mortality of the animals was determined. The results are shown in Table 2.

As shown in Table 2, the novel antitumorally active polypeptide has a low lethal action on mice. In terms of the amount which caused death of 50% of the mice, the lethal action of the novel antitumorally active polypeptide was about 1/20 of that of the human TNF protein and about 1/16 of that of the N-terminus deleted human TNF protein.

When these lethal actions are considered together with the specific activity values indicated in Table 1 of Example 7, the novel antitumorally active polypeptide is about 130 times as advantageous as the human TNF protein.

Furthermore, when they are considered together with the specific activity values described in Japanese Laid-Open Patent Publication No. 248498/1987, the novel antitumorally active polypeptide is about 37 times as advantageous as the N-terminus deleted human TNF protein both with regard to specific activity and lethal action.

TABLE 2

| | Number mice dead/number of mice tested | | |
|---|---|---|---|
| Dose (microgram per head) | Human TNF protein | TNF resulting from deleting 7 amino acids | Novel antitumorally active polypeptide |
| 0.1 | 5/10 | 2/10 | 0/5 |
| 0.4 | 10/13 | 10/10 | 1/5 |
| 1.6 | 9/11 | 5/5 | 2/5 |
| 6.4 | 11/11 | 5/5 | 4/5 |

TABLE 2-continued

| Dose (microgram per head) | Number mice dead/number of mice tested | | |
|---|---|---|---|
| | Human TNF protein | TNF resulting from deleting 7 amino acids | Novel anti-tumorally active poly-peptide |
| 25.6 | 8/8 | 4/4 | 3/5 |

EXAMPLE 10

Evaluation of Antitumor Activity In Vivo

The antitumor activity in vivo of the novel antitumorally active polypeptide was measured by the method of Carswell et al. cited above. Specifically, $5 \times 10^5$ Meth A sarcoma cells were suspended in 50 miroliters of RPMI 1640 medium (Nissui), and transplanted into the subcutaneous area in the side part of the abdomen of BALB/C mice (6 to 8 weeks old, male, Charles River). On the 7th to 19th days after transplantation when the tumor diameter reached 6 to 10 mm, 10 micrograms of the novel physiologically active polypeptide prepared in Example 8 was administered into the tail vein. Within 24 hours after administration, a bled and necrotized pattern was observed on the surface of the tumor. This shows that the novel antitumorally active polypeptide of this invention also has marked antitumor activity in vivo. An example of the tumor carrying mouse of which tumor was bled and necrotized is shown in FIG. 12.

The black part 1 in FIG. 12 shows the bled and necrotized portion.

In the same way as above, 10 micrograms of the novel antitumorally active polypeptide, the human TNF protein, or physiological saline was administered into the tail vein of tumor-bearing mice, and the degrees of necrosis after 24 hours were compared in accordance with the method of Carswell et al. cited above. The results are shown in Table 3. It is seen from Table 3 that the novel antitumorally active polypeptide has higher activity than the human TNF protein in vivo as well as in vitro.

TABLE 3

| | Degree of necrosis (number) | | | |
|---|---|---|---|---|
| | − | + | ++ | +++ |
| Control (saline) | 10 | 0 | 0 | 0 |
| Human TNF protein | 0 | 5 | 2 | 0 |
| Novel antitumorally active polypeptide | 0 | 1 | 5 | 4 |

Furthermore, 2 micrograms or 10 micrograms of the novel antitumorally active polypeptide or physiological saline was administered over 7 consecutive days once a day, and the changes of the relative tumor weight with time was examined. The results are shown in FIG. 13.

In FIG. 13, the tumor weight was calculated from the equation $\frac{1}{2} \times$ (long diameter of the tumor) $\times$ (short diameter of the tumor)$^2$. It is seen from FIG. 13 that at a dose of 2 micrograms/shot, the proliferation of the tumor was inhibited to about half, and at a dose of 10 micrograms/shot, the proliferation was inhibited nearly completely.

In calculating the relative tumor weight, the outside diameter of the tumor was measured. Actually, more than 50% of the tumor was bled and necrotized. Hence, if the weight corresponding to the necrotized portion is subtracted from the relative tumor weight, the curative effect of the novel antitumorally active polypeptide is much higher than that shown in FIG. 13.

EXAMPLE 11

Preparation of pTNF472 and pTNF601 Capable of Expressing the Novel Antitumorally Active Polypeptide Expression plasmid pTNF472 was prepared in the same way as in Example 5 except that the synthetic oligonucleotides shown in FIG. 14 were used instead of the synthetic oligonucleotides shown in FIG. 9. This plasmid encodes a novel antitumorally active polypeptide having the following amino acid sequence.

(H2N)—Arg—Lys—Arg—Lys—
Pro—Val—Ala—His—Val—Val—Ala—
Asn—His—Gln—Ala—Glu—Gly—Gln—
Leu—Gln—Trp—Leu—Asn—Arg—Arg—
Ala—Asn—Ala—Leu—Leu—Ala—Asn—
Gly—Val—Glu—Leu—Arg—Asp—Asn—
Gln—Leu—Val—Val—Pro—Ser—Glu—
Gly—Leu—Tyr—Leu—Ile—Tyr—Ser—
Gln—Val—Leu—Phe—Lys—Gly—Gln—
Gly—Cys—Pro—Ser—Thr—His—Val—
Leu—Leu—Thr—His—Thr—Ile—Ser—
Arg—Ile—Ala—Val—Ser—Tyr—Gln—
Thr—Lys—Val—Asn—Leu—Leu—Ser—
Ala—Ile—Lys—Ser—Pro—Cys—Gln—
Arg—Glu—Thr—Pro—Glu—Gly—Ala—
Glu—Ala—Lys—Pro—Trp—Tyr—Glu—
Pro—Ile—Tyr—Leu—Gly—Gly—Val—
Phe—Gln—Leu—Glu—Lys—Gly—Asp—
Arg—Leu—Ser—Ala—Glu—Ile—Asn—
Arg—Pro—Asp—Tyr—Leu—Asp—Phe—
Ala—Glu—Ser—Gly—Gln—Val—Tyr—
Phe—Gly—Ile—Ile—Ala—Leu—
(COOH)

The plasmid pTNF401A capable of expressing the human TNF gene obtained in Example 4 (20 micrograms) was dissolved in 100 microliters of an aqueous solution containing 10 mM Tris-HCl (pH 7.4), 10 mM of MgSO$_4$ and 1 mM dithiothreitol, and 40 units of restriction endonuclease KpnI (a product of Takara Shuzo) was added, and the digestion reaction was carried out at 37° C. for 1 hour. Furthermore, as in Example 3, digestion with restriction endonuclease ClaI was carried out, followed by polyacrylamide gel electrophoresis (gel concentration 5%) and agarose gel electrophoresis (gel concentration 0.8%). In accordance with the methods of Examples 2 and 3 respectively, the resulting two DNA fragments (about 160 bp and about 3.0 kbp; both were ClaI - KpnI fragments) were recovered from the gels.

The resulting DNA fragment (about 160 bp) containing the first half of the human TNF gene was dissolved in 50 microliters of an aqueous solution containing 10 mM Tris-HCl (pH 7.4), 10 mM MgSO$_4$ and 1 mM dithiothreitol, and 10 units of restriction endonuclease HapII (a product of Takara Shuzo) was added. The digestion reaction was carried out at 37° C. for 1 hour. After the reaction, the digestion product was electrophoresed on a polyacrylamide gel (gel concentration 5%), and in accordance with the method of Example 2, a DNA fragment having a size of about 100 bp (ClaI - HapII) containing the first half of the human TNF gene was recovered from the polyacrylamide gel.

Oligonucleotides having the base sequence shown in FIG. 15 were synthesized and purified in accordance with the method of Example 2. Phosphorylation of the terminal was carried out as in Example 3 on 0.5 microgram of each of the resulting two synthetic oligonucleotides and then annealing was carried out.

After the reaction, the resulting double-stranded oligonucleotides was mixed with the DNA fragment having a size of about 3.0 kbp obtained above (ClaI - KpnI) and the DNA fragment having a size of about 100 bp and containing the first half of the human TNF gene (ClaI - HapII), and after ethanol precipitation, the DNA fragments were ligated with T4-DNA ligase by the same method as in Example 3. After the reaction, the ligated DNA was introduced into *E. coli* C600r-m- strain as in Example 3, and clones having the desired plasmid pTNF489 (about 3.2 kbp) were selected from the transformants. This plasmid encodes a novel antitumorally active polypeptide having the following amino acid sequence. FIG. 15-B shows a method of preparing it.

(H₂N)—Val—Arg—Ser—Ser—
Ser—Arg—Thr—Pro—Ser—Asp—Lys—
Pro—Val—Ala—His—Val—Val—Ala—
Asn—Pro—Gln—Ala—Glu—Gly—Gln—
Leu—Gln—Trp—Leu—Asn—Arg—Arg—
Ala—Asn—Ala—Leu—Leu—Ala—Asn—
Gly—Val—Glu—Leu—Arg—Asn—Asn—
Ser—Leu—Val—Val—Pro—Ser—Glu—
Gly—Leu—Tyr—Leu—Ile—Tyr—Ser—
Gln—Val—Leu—Phe—Lys—Gly—Gln—
Gly—Cys—Pro—Ser—Thr—His—Val—
Leu—Leu—Thr—His—Thr—Ile—Ser—
Arg—Ile—Ala—Val—Ser—Tyr—Gln—
Thr—Lys—Val—Asn—Leu—Leu—Ser—
Ala—Ile—Lys—Ser—Pro—Cys—Gln—
Arg—Glu—Thr—Pro—Glu—Gly—Ala—
Glu—Ala—Lys—Pro—Trp—Tyr—Glu—
Pro—Ile—Tyr—Leu—Gly—Gly—Val—
Phe—Gln—Leu—Glu—Lys—Gly—Asp—
Arg—Leu—Ser—Ala—Glu—Ile—Asn—
Arg—Pro—Asp—Tyr—Leu—Asp—Phe—
Ala—Glu—Ser—Gly—Gln—Val—Tyr—
Phe—Gly—Ile—Ile—Ala—Leu—
(COOH)

The plasmid pTNF471 obtained in Example 5 was digested with the restriction endonucleases ClaI, HindIII and HapII by the method of Example 4 and the above method to give a DNA fragment having a size of about 80 bp (ClaI - HapII). This DNA fragment, a DNA fragment (ClaI - HindIII) having a size of about 2.7 bp obtained by digesting the plasmid pTNF489 with ClaI and HindIII, and a DNA fragment (HapII - HindIII) having a size of about 390 bp obtained by digesting the plasmid pTNF489 with ClaI, HindIII and HapII were ligated and introduced into *E. coli* C600r-m- strain in the same way as in Example 3. Clones having the desired plasmid pTNF601 (about 3.2 kbp) were selected from the transformants. This plasmid encodes a novel antitumorally active polypeptide having the following amino acid sequence. FIG. 16 shows a method of preparing this plasmid.

(H₂N)—Arg—Lys—Arg—Lys—
Pro—Val—Ala—His—Val—Val—Ala—
Asn—Pro—Gln—Ala—Glu—Gly—Gln—
Leu—Gln—Trp—Leu—Asn—Arg—Arg—
Ala—Asn—Ala—Leu—Leu—Ala—Asn—
Gly—Val—Glu—Leu—Arg—Asn—Asn—
Ser—Leu—Val—Val—Pro—Ser—Glu—
Gly—Leu—Tyr—Leu—Ile—Tyr—Ser—
Gln—Val—Leu—Phe—Lys—Gly—Gln—
Gly—Cys—Pro—Ser—Thr—His—Val—
Leu—Leu—Thr—His—Thr—Ile—Ser—
Arg—Ile—Ala—Val—Ser—Tyr—Gln—
Thr—Lys—Val—Asn—Leu—Leu—Ser—

-continued
Ala—Ile—Lys—Ser—Pro—Cys—Gln—
Arg—Glu—Thr—Pro—Glu—Gly—Ala—
Glu—Ala—Lys—Pro—Trp—Tyr—Glu—
Pro—Ile—Tyr—Leu—Gly—Gly—Val—
Phe—Gln—Leu—Glu—Lys—Gly—Asp—
Arg—Leu—Ser—Ala—Glu—Ile—Asn—
Arg—Pro—Asp—Tyr—Leu—Asp—Phe—
Ala—Glu—Ser—Gly—Gln—Val—Tyr—
Phe—Gly—Ile—Ile—Ala—Leu—
(COOH)

EXAMPLE 12

Determination of Expression and Evaluation of In Vitro Antitumor Activity

A lysate was prepared as in Example 6 from the *E. coli* C600r-m- strain containing the plasmid pTNF472 or pTNF601 obtained in Example 11. The lysate was electrophoreses on an SDS-polyacrylamide gel, and it was confirmed that these plasmids expressed the novel antitumorally active polypeptide gene.

In accordance with the method of Example 7, the in vitro antitumor activity of the lysate containing the novel antitumorally active polypeptide was measured, and its specific activity was calculated. The results are shown in Table 4.

TABLE 4

| Physiolocally active polypeptide | Plasmid | Ratio of specific activity |
| --- | --- | --- |
| Human TNF protein | pTNF401A | 1.0 |
| Novel antitumorally active polypeptide | pTNF472 | 3.0 |
|  | pTNF601 | 6.7 |

We claim:
1. An antitumor active polypeptide having the following amine acid sequence

NH₂—(Met)ₙ—Arg—Lys—Arg—Lys—
Pro—Val—Ala—His—Val—Val—Ala—
Asn—Pro—Gln—Ala—Glu—Gly—Gln—
Leu—Gln—Trp—Leu—Asn—Arg—Arg—
Ala—Asn—Ala—Leu—Leu—Ala—Asn—
Gly—Val—Glu—Leu—Arg—Asp—Asn—
Gln—Leu—Val—Val—Pro—Ser—Glu—
Gly—Leu—Tyr—Leu—Ile—Tyr—Ser—
Gln—Val—Leu—Phe—Lys—Gly—Gln—
Gly—Cys—Pro—Ser—Thr—His—Val—
Leu—Leu—Thr—His—Thr—Ile—Ser—
Arg—Ile—Ala—Val—Ser—Tyr—Gln—
Thr—Lys—Val—Asn—Leu—Leu—Ser—
Ala—Ile—Lys—Ser—Pro—Cys—Gln—
Arg—Glu—Thr—Pro—Glu—Gly—Ala—
Glu—Ala—Lys—Pro—Trp—Tyr—Glu—
Pro—Ile—Tyr—Leu—Gly—Gly—Val—
Phe—Gln—Leu—Glu—Lys—Gly—Asp—
Arg—Leu—Ser—Ala—Glu—Ile—Asn—
Arg—Pro—Asp—Tyr—Leu—Asp—Phe—
Ala—Glu—Ser—Gly—Gln—Val—Tyr—
Phe—Gly—Ile—Ile—Ala—Leu—
COOH in which n represents 0 or 1, NH₂ represents the amino-terminus, and COOH represents the carboxy-terminus.

2. A pharmaceutical composition comprising an effective amount of an antitumor active and a pharmaceutically acceptable carrier polypeptide having the amino acid sequence of claim 1 as an active ingredient.

3. An antitumor injecting composition consisting essentially of an effective amount of an antitumor active polypeptide having the amino acid sequence of claim 1 and an inert liquid carrier.

4. An antitumor active polypeptide having the following amino acid sequence $NH_2$—(Met)$_n$—Arg—Lys—Arg—Lys—
Pro—Val—Ala—His—Val—Val—Ala—

Asn—[Pro]$^{*1}$—Gln—Ala—Glu—Gly—Gln—

Leu—Gln—Trp—Leu—Asn—Arg—Arg—
Ala—Asn—Ala—Leu—Leu—Ala—Asn—

Gly—Val—Glu—Leu—Arg—[Asp]$^{*2}$—Asn

[Gln]$^{*3}$—Leu—Val—Val—Pro—Ser—Glu—
Gly—Leu—Tyr—Leu—Ile—Tyr—Ser—
Gln—Val—Leu—Phe—Lys—Gly—Gln—

-continued
Gly—Cys—Pro—Ser—Thr—His—Val—
Leu—Leu—Thr—His—Thr—Ile—Ser—
Arg—Ile—Ala—Val—Ser—Tyr—Gln—
Thr—Lys—Val—Asn—Leu—Leu—Ser—
Ala—Ile—Lys—Ser—Pro—Cys—Gln—
Arg—Glu—Thr—Pro—Glu—Gly—Ala—
Glu—Ala—Lys—Pro—Trp—Tyr—Glu—
Pro—Ile—Tyr—Leu—Gly—Gly—Val—
Phe—Gln—Leu—Glu—Lys—Gly—Asp—
Arg—Leu—Ser—Ala—Glu—Ile—Asn—
Arg—Pro—Asp—Tyr—Leu—Asp—Phe—
Ala—Glu—Ser—Gly—Gln—Val—Tyr—
Phe—Gly—Ile—Ile—Ala—Leu—
COOH in which n represents 0 or 1, $NH_2$ represents the amino-terminus, COOH represents the carboxy-terminus, and at least one amino acid among the asterisked amino acids are replaced independently from each other such that Pro$^{*1}$ is replaced by His, Asp$^{*2}$ is replaced by Asn, and Gln$^{*3}$ is replaced by Ser.

* * * * *